(12) United States Patent
Beckwith et al.

(10) Patent No.: US 7,410,788 B2
(45) Date of Patent: Aug. 12, 2008

(54) COMPOSITIONS AND METHODS FOR PRODUCTION OF DISULFIDE BOND CONTAINING PROTEINS IN HOST CELLS

(75) Inventors: Jonathan Beckwith, Cambridge, MA (US); Fredrik Aslund, Stockholm (SE); Paul H. Bessette, Camarillo, CA (US); George Georgiou, Austin, TX (US); Daniel Ritz, Everett, MA (US); Jackie Eun-ah Lim, Shrewsbury, MA (US)

(73) Assignees: President and Fellows of Harvard College, Cambridge, MA (US); Board of Regents, University of Texas System, Austin, TX (US)

( * ) Notice: Subject to any disclaimer, the term of this patent is extended or adjusted under 35 U.S.C. 154(b) by 0 days.

(21) Appl. No.: 11/058,926

(22) Filed: Feb. 16, 2005

(65) Prior Publication Data

US 2006/0030022 A1    Feb. 9, 2006

Related U.S. Application Data

(63) Continuation of application No. 09/679,705, filed on Oct. 5, 2000, now Pat. No. 6,872,563.

(60) Provisional application No. 60/166,044, filed on Nov. 17, 1999, provisional application No. 60/163,939, filed on Nov. 8, 1999, provisional application No. 60/157,770, filed on Oct. 5, 1999.

(51) Int. Cl.
*C12N 1/21* (2006.01)
*C12N 7/00* (2006.01)
*C12P 21/00* (2006.01)
*C12N 15/63* (2006.01)

(52) U.S. Cl. .................. 435/252.3; 435/252.1; 435/71.1
(58) Field of Classification Search .................. None
See application file for complete search history.

(56) References Cited

U.S. PATENT DOCUMENTS 6,872,563 B1    3/2005    Beckwith et al.

OTHER PUBLICATIONS

Nawrocki et al. Reduction of LDL Cholesterol by 25% to 60% in Patients with Primary Hypercholesterolemia by Atorvastin, a New HMG-CoA Reductase Inhibitor. Arterioscier Thromb Vasc Biol. 15: 678-682, 1995.*
Thorstenson et al. Leaderless Polypeptides Efficiently Extracted form Whole Cells by Osmotic Shock. J. Bac. 179(17): 5333-5339, 1997.*
Wunderlich et al. Redox properties of protein disulfide isomerase (DsbA) from *Escherichia coli*. Protein Sci. 2: 717-726, 1993.*
Aslund, F. et al. (1999), *Efficient Production of Disulfide Bonded Proteins in the Cytoplasm in "Oxidizing" Mutants of E. coli*, InNovations 10:11-12 (http://www.novagen.com/SharedImages.Technical-Literature/17$_{13}$nd0d.pdf).
Mossner, E. et al. (1998), *Characterization of Escherichia coli Thioredoxin Variants Mimicking the Active-Sites of Other Thiol/Disulfide Oxidoreductases*, Protein Science 7:1233-44.
Martin, J. (1995), *Thioredoxin—A Fold For All Reasons*, Structure 3:245-50.
Aslund, F. et al (1999), *The Thioredoxin Superfamily: Redundancy, Specificity, and Gray-Area Genomics*, J. of Bacteriology 181(5):1375-79.
Aslund, F. et al. (1999), *Regulation of the OxyR Transcription Factor by Hydrogen Peroxide and the Cellular Thiol—Disulfide Status*, Proc. Natl. Acad. Sci. USA 96:6161-65.
Mossner, E. et al. (1999), *Importance of Redox Potential for the in Vivo Function of the Cytoplasmic Disulfide Reductant Thioredoxin from Escherichia coli*, J. Biol. Chem. 274(36):25254-59.
Rietsch, A. et al. (1998), *The Genetics of Disulfide Bond Metabolism*, Annu. Rev. Genet. 32:163-84.
Derman, A. et al. (1993), *Mutations that Allow Disulfide Bond Formation in the Cytoplasm of Escherichia coli*, Science 262:1744-47.
Qiu, J. et al. (1998), *Expression of Active Human Tissue-Type Plasminogen Activator in Escherichia coli*, Applied and Environ. Microbiol. 64(12):4891-96.
Stewart, E.J. et al. (1998), *Disulfide Bond Formation in the Escherichia coli cytoplasm: an in vivo Role Reversal for the Thioredoxins*, EMBO J. 17(19):5543-50.
Prinz, W. A. et al. (1997), *The Role of the Thioredoxin and Glutaredoxin Pathways in Reducing Protein Disulfide Bonds in the Escherichia coli Cytoplasm*, J. Biol. Chem. 272(25):15661-67.
Debarbieux, L. et al. (1998), *The Reductive Enzyme Thioredoxin 1 Acts as an Oxidant When it is Exported to the Escherichia coli Periplasm*, Proc. Natl. Acad. Sci. USA 95:10751-56.
Aslund, F. et al. (1997), *Redox Potentials of Glutaredoxins and Other Thiol-Disulfide Oxidoreductases of the Thioredoxin Superfamily Determined by Direct Protein-Protein Redox Equilibria*, J. Biological Chem. 272(49):30780-86.
Jordan, A. et al. (1997), *Characterization of Escherichia coli NrdH*, J. Biological Chem. 272(29):18044-50.
Aslund, F. et al. (1996), *Glutaredoxin-3 from Escherichia coli*, J. of Biological Chem. 271(12):6736-45.
Bessette, P.H. et al. (Nov. 23, 1999), *Efficient Folding of Proteins with Multiple Disulfide Bonds in the Escherichia coli Cytoplasm*, PNAS 96(24):13703-08.

(Continued)

*Primary Examiner*—Nancy Vogel
*Assistant Examiner*—Michele K. Joike
(74) *Attorney, Agent, or Firm*—Foley Hoag LLP

(57) ABSTRACT

The invention provides composition and methods for producing proteins of interest which comprise at least one disulfide bond, include proteins which in their mature form do not contain disulfide bonds, but whose precursor molecule contained at least one disulfide bond. The methods employ a host cell modified to more efficiently produce properly folded disulfide bond containing proteins. The host cells generally contain a mutation in one or more reductase genes, and can be further genetically modified to increase their growth rate, and are further optionally modified to increase the expression of a catalyst of disulfide bond formation. Host cells, methods for using such to produce proteins of interest, proteins of interest produced by these methods are within the scope of the invention.

39 Claims, 11 Drawing Sheets

OTHER PUBLICATIONS

Ritz, D. et al. (1999), *Thioredoxin 2 is Involved in the Oxidative Stress Response in Escherichia coli*, J. Bio. Chem. 275:2505-12.

Debarbieux, L. et al. (2000), *On the Functional Interchangeability, Oxidanmt versus Reductant, of Members of the Thioredoxin Superfamily*, J. of Bacteriology 182(3):723-27.

Aslund, F. et al. (1999), *Bridge Over Troubled Waters: Sensing Stress by Disulfide Bond Formation*, Cell 96:751-53.

Kurokawa, Y. et al. (2000), *Overexpression of Protein Disulfide Isomerase DsbC Stabilizes Multiple-Disulfide-Bonded Recombinant Protein Produced and Transported to the Periplasm in Escherichia coli*, Applied and Environmental Microbiology 66(9):3960-65.

Ferrante, A. A, et al. (1995), *Cloning of an organic solvent-resistance gene in Escherichia coli: The unexpected role of alkylhydroperxide reductase*, Applied Biological Sciences 92:7617-21.

Ritz, D. et al. (2001), *Conversion of a Peroxiredoxin into a Disulfide Reductase by a Triplet Repeat Expansion*, Science 294:158-160.

Mittl, P. and Schulz, G. (1994), Structure of glutathione reductase from *Escherichia coli* at 1.86 Å resolution: Comparison with the enzyme from human erythrocytes, Protein Science 3: 799-809.

Romero, M. and Canada, A. (1991), The Evaluation of *Escherichia coli* as a model for Oxidant Stress in Mammalian Hepatocytes: Role of Glutathione, Toxicology and Applied Pharmacology, 111: 485-495.

Schallreuter, K. and Wood, J.M. (1987), Azelaic acid as a comptetive inhibitor of thioredoxin reductase in human melanoma cells, Cancer Letters, 36: 297-305.

Waksman, G. et al. (1994), Crystal Structure of *Escherichia coli* Thioredoxin Reductase refined at 2 Å Resolution, J. Mol. Biol., 236: 800-816.

Ellis, H.R., et al. (1997), Roles For The Two Cysteine Residues of AhpC in Catalysis of Peroxide Reduction by Alkyl Hydroperoxide Reductase from *Salmonella typhimurium*.

\* cited by examiner

Figure 1
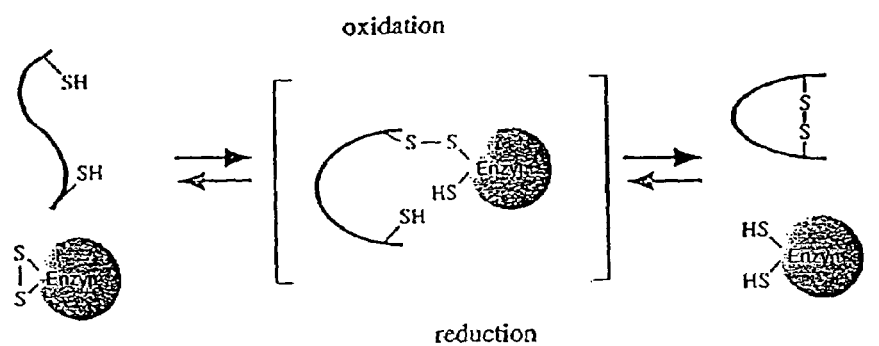
oxidation
reduction
Disulfide Bond Isomerization
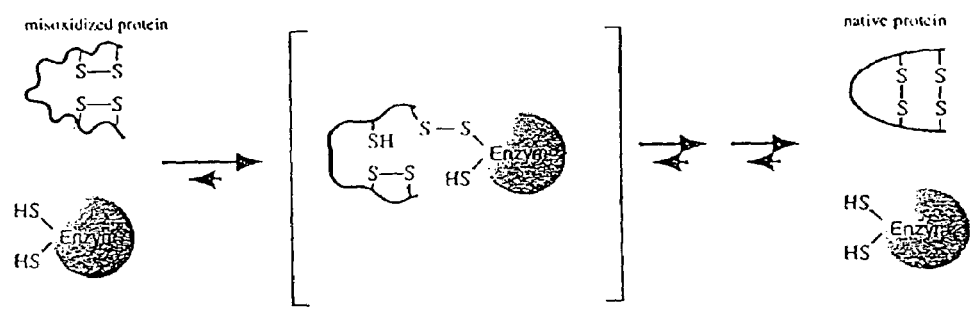

Figure 8

A triplet insertion in a ahpC restores growth to a trxB gor double mutant wt AhpC

```
TGGAGCGTCTTCTTCTACCCGGCTGACTTTACTTTCGTATGCCCG
 W  S  V  F  F  Y  P  A  D  F  T  F  V  C  P
 33                                        47
```

AhpC*

```
TGGAGCGTCTTCTTCTTCTACCCGGCTGACTTTACTTTCGTATGCCCG
 W  S  V  F  F  F  Y  P  A  D  F  T  F  V  C  P
 33                                           48
```

A

B

| | | |
|---|---|---|
| E. coli | 32 | RWSVFFFYPADFTFVCPTELGDVADHYEELQK |
| S. typhi | 32 | RWSVFFFYPADFTFVCPTELGDVADHYEELQK |
| P. putida | 32 | KWSVVFFYPADFTFVCPTELGDLADNYAEFQK |
| S. mutans | 32 | KWAVFCFYPADFSFVCPTELGDLQEQYATLQS |
| B. subtilis | 32 | QWSVFCFYPADFSFVCPTELEDLQEQYAALKE |
| S. aureus | 34 | SWSVVCFYPADFTFVCPTELEDLQNQYEELQK |
| T. pallidum | 33 | SWAVFMFYPADFTFVCPTELADLARVYPSFVE |
| A. aeolicus | 50 | KWVILFEYPADYTFVCPTELADLAEKYDELKE |
| HUMAN_TPA | 36 | KYVVLFFYPLDFTFVCPTEIIAFTTVKRTSAK |

Depending on the oxidative stress-inducing signal two different forms of AhpC can be found

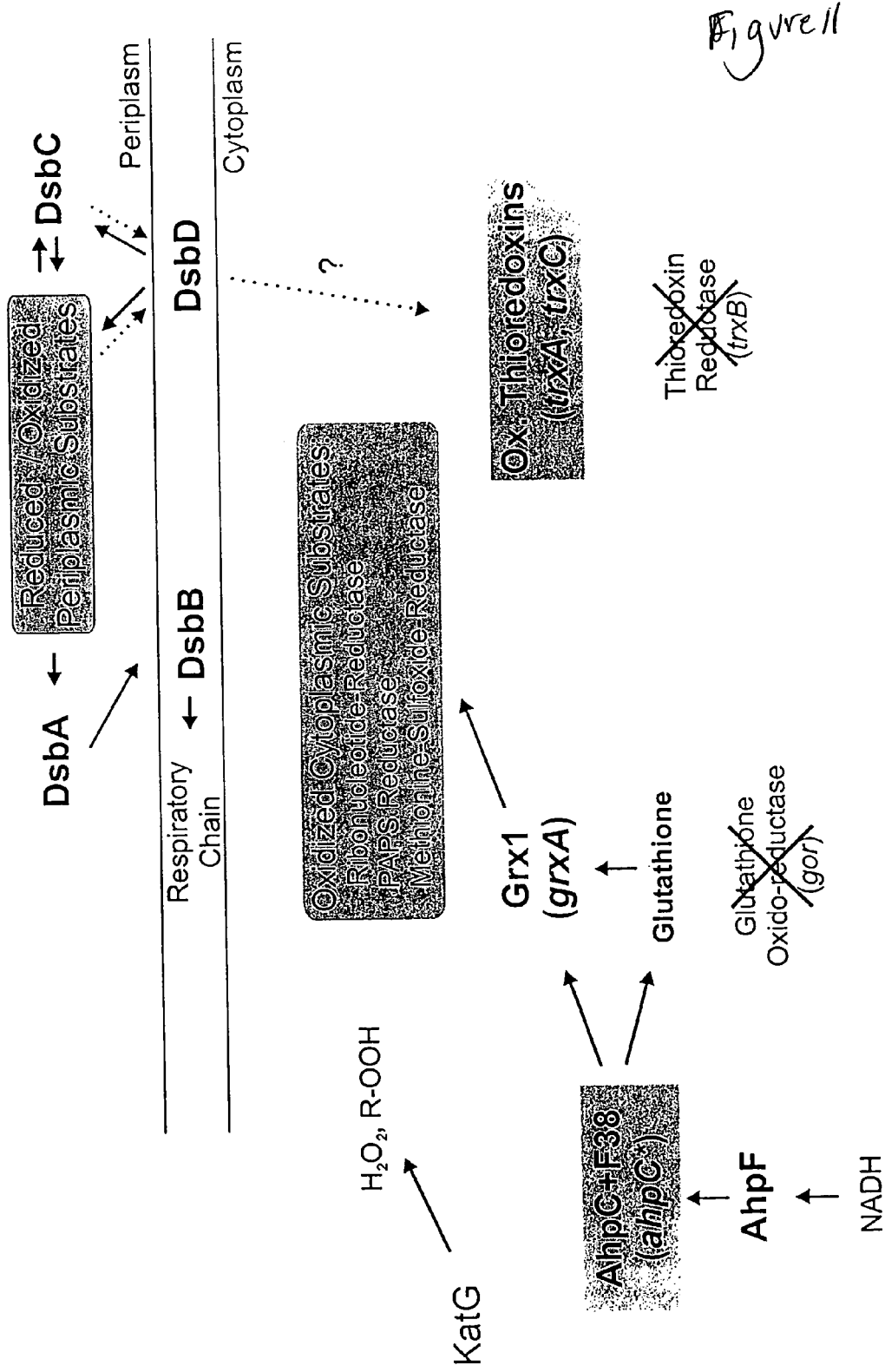

COMPOSITIONS AND METHODS FOR PRODUCTION OF DISULFIDE BOND CONTAINING PROTEINS IN HOST CELLS

CROSS-REFERENCE TO RELATED APPLICATIONS

This application is a continuation of U.S. patent application Ser. No. 09/679,705, filed on Oct. 5, 2000 now U.S. Pat. No. 6,872,563; which claims the benefit of priority to U.S. Provisional Application No. 60/157,770, filed Oct. 5, 1999; U.S. Provisional Application No. 60/163,939, filed Nov. 8, 1999; and U.S. Provisional Application No. 60/166,044, filed Nov. 17, 1999, the contents of which are specifically incorporated herein.

STATEMENT OF RIGHTS

This invention was made during the course of work supported by NIH 5RO1 GM55090-02. Thus, the U.S. Government has certain rights in the invention.

BACKGROUND OF THE INVENTION

Overexpression of many secreted proteins which are stabilized by disulfide bonds cannot be obtained by mere expression in bacterial host cells, due at least to the reducing cytoplasm of E. coli. Such proteins either become degraded or are found insoluble in so-called inclusion bodies. This problem is often addressed by alternative expression strategies such as export of the protein to the periplasm of E. coli or expression in another organism. These strategies are laborious, requiring the recloning of genes of interest in other vectors. In addition, certain proteins of particular interest, e.g., pharmacological interest, cannot currently be produced at high levels an in active form in bacteria.

The following is a summary of the current knowledge in the art regarding the synthesis of disulfide bond containing proteins. The fundamental discovery that a denatured protein, ribonuclease, could assemble correctly in the absence of any catalysts indicated that all the information for the proper folding of a protein was present in its primary amino acid sequence. Since disulfide bonds are necessary for the proper folding of ribonuclease, these experiments were also taken to mean that disulfide bond formation was independent of enzyme catalysts. Thus, it had been presumed that only the presence of oxygen (or small molecules such as oxidized glutathione) is needed in vivo for disulfide bond formation. This presumption appeared to explain the fact that proteins with structural disulfide bonds are only found in the more oxidizing non-cytosolic intracellular compartments or in the extracellular space. According to this view, disulfide bonds do not form in the cytosol simply because the reducing components such as glutathione and thioredoxins keep such bonds reduced.

The first modification of this view of disulfide bond formation and the basis for its compartmentalization came from the finding that disulfide bond formation in gram-negative bacteria does require the presence of a protein catalyst, DsbA (Bardwell, et al. (1991) Cell 67: 581; Kamitani, et al. (1992) EMBO J. 11: 57; Peek, et al. (1992) Proc Natl Acad Sci USA 89: 6210; Tomb, J. F. (1992) Proc Nail Acad Sci USA 89: 10252; Yu, et al. (1992) Mol. Microbiol. 6: 1949). This finding not only changed the picture of how disulfide bond formation takes place normally, but also raised questions about the basis for the absence of disulfide bonds in cytosolic proteins. Normally, the formation of stable disulfide bonds in the cytoplasm is an exceedingly rare event (Locker & Griffiths, (1999) J. Cell Biol. 144: 267). Transient disulfide bonds that are not required for the stability of the native state have been detected in a few cytoplasmic proteins that include enzymes such as ribonucleotide reductase, the transcription factors OxyR and RsrA, the Hsp33 chaperone, and in a partially folded intermediate of the P22 tailspike endorhamnosidase (Aslund, et al. (1999) Proc Nail Acad Sci USA 96: 6161; Robinson & King (1997) Nat. Struct. Biol. 4: 450; Kang, et al. (1999) EMBO J. 18: 4292 and Jakob et al. (1999) Cell 96:341). In general, the oxidation of cysteine thiols in cytoplasmic proteins is strongly disfavored for both thermodynamic and kinetic reasons. First of all, the thiol-disulfide redox potential of the cytoplasm is too low to provide a sufficient driving force for the formation of stable disulfides. Second, under physiological conditions, there are no enzymes that can catalyze protein thiol oxidation. The E. coli cytoplasm contains two thioredoxins, TrxA and TrxC, and three glutaredoxins (Rietsch & Beckwith (1998) Annu. Rev. Genet. 32: 163; Aslund & Beckwith (1999) J. Bacteriol. 181: 1375). The oxidized form of these proteins can catalyze the formation of disulfide bonds in peptides. However, in the cytosol both the thioredoxins and the glutaredoxins are maintained in a reduced state by the action of thioredoxin reductase (TrxB) and glutathione, respectively. In E. coli, glutathione is synthesized by the gshA and gshB gene products. The enzyme glutathione oxidoreductase, the product of the gor gene, is required to reduce oxidized glutathione and complete the catalytic cycle of the glutathione-glutaredoxin system.

In a trxB null mutant, stable disulfide bonds can form in normally secreted proteins, such as alkaline phosphatase, when they are expressed in the cytoplasm without a signal sequence. Subsequent studies revealed that in a trxB mutant, the two thioredoxins are oxidized and serve as catalysts for the formation of disulfide bonds (Stewart, et al. (1998) EMBO J. 17: 5543). Disulfide bond formation was found to be even more efficient in double mutants defective in both the thioredoxin (trxB) and glutathione (gor or gshA) pathways (Prinz, et al. (1997) J. Biol. Chem. 272: 15661). Double mutants, trxB gor or trxB gshA, grow very poorly (doubling time over 300 minutes) and require an exogenous reductant such as dithiothreitol (DTT) to achieve a reasonable growth rate.

In view of the numerous proteins of biotechnological and pharmaceutical interest, that are complex molecules containing multiple disulfide bonds, such as the tissue plasminogen activator (tPA), it would be highly desirable to have an efficient method of production of complicated proteins which retain their biological activity. In addition, since expression of recombinant proteins in bacteria is generally a method of choice, but that the formation of disulfide bonds in recombinant proteins expressed in bacteria has been very inefficient, it would be highly desirable to have a prokaryotic system, e.g., bacterial system that allows efficient expression of recombinant proteins containing multiple disulfide bonds. Such a method would be commercially important, at least in part, to produce therapeutics. For example, tPA, is a widely used therapeutic agent with sales exceeding $400 million per year. However, tPA is currently produced in mammalian cells which are costly to grow, resulting in very high price for the drug (well over $1,000 per dose). Cheaper methods of manufacturing therapeutic proteins would result in increased availability of the drug, to the benefit of many more patients.

SUMMARY OF THE INVENTION

The invention pertains to compositions and methods for producing proteins of interest containing at least one disulfide bond. The invention is based at least in part on the observation that active recombinant proteins containing a high number of disulfide bonds can be efficiently produced in the cytoplasm of modified prokaryotic cells.

In one embodiment, the invention provides a host cell that is genetically modified to shift the redox status of its cytoplasm to a more oxidative state. In a preferred embodiment, the host cell further contains a gene encoding a catalyst of disulfide bond formation and/or isomerization. The host cell is preferably a prokaryotic cell, but can also be a eukaryotic cell, e.g., a yeast cell. In a preferred embodiment, the expression or activity of a reductase in the host cell is decreased relative to that in the corresponding wild type cell. The reductase can be selected from the group consisting of thioredoxin reductase, glutathione reductase, and glutathione. In an even more preferred embodiment, the expression or activity of a second reductase is decreased relative to that in the corresponding wild type cell. The second reductase can also be selected from the group consisting of thioredoxin reductase, glutathione reductase, and glutathione.

In a much preferred embodiment, the gene encoding the reductase is mutated, e.g., the gene contains a null mutation, resulting in the complete absence of the gene product. A preferred host cell comprises a null mutation in the thioredoxin reductase gene and in the glutathione reductase gene. Alternatively, the activity of one or more reductases is inhibited, e.g., by contacting the prokaryotic cell with an agent.

In yet another preferred embodiment, the host cell is further modified to increase its ability to proliferate. The modification can, e.g., increase the reducing capacity of the cytoplasm sufficiently to increase the growth of the host cell. The modification can be a mutation in a gene, e.g., a suppressor mutation, or it can an introduction and expression of a gene encoding a growth promoting protein into the host cell. In a preferred embodiment, the gene encoding the AphC subunit of the alkyl hydroperoxidase is mutated in the host cell, e.g., by the presence of a mutation in the TCT triplet rich region of the gene (see FIG. 8A). In another embodiment, a gene encoding a mutated form of AphC is introduced and expressed in the host cell. Such host cells preferably have a growth curve that is similar to that of the wild type parent strain. Particularly preferred host cells are the host cells described in the Examples, referred to as FA112 and FA113, which are trxB gsha supp and trxB gor supp mutants, respectively. These two strains have been deposited at the American Type Culture Collection (ATCC) 10801 University Blvd., Manassas, Va. 20110-2209 on Nov. 11, 1999, in accordance with the terms and provisions of the Budapest Treaty relating to the deposit of microorganism. FA112 and FA113 have been assigned ATCC Accession No. PTA-938 and PTA-939, respectively.

The host cell can comprise a nucleic acid encoding a catalyst of disulfide bondr isomerization, e.g., variants of a thioredoxin or glutaredoxin, which have, e.g., a redox potential that is higher than that of its wild type counterpart. In an illustrative example, the variant is a "Grx" variant of thioredoxin A. The host cell can also comprise a catalyst of disulfide bond isomerization, such as a disulfide bond isomerase, e.g., DsbC, or derivative thereof.

In another embodiment, the invention provides a host cell, e.g., a prokaryotic host cell, that is genetically modified to shift is redox status in the cytoplasm to a more oxidative state, and which further contains a genetic modification to increase its ability to proliferate. Modification of the oxidative state of its cytoplasm can be achieved by decreasing the level or activity of one or more reductases, e.g., thioredoxin reductase, glutathione reductase, and glutathione, as described above. The modification to increase its ability to proliferate can be a suppressor mutation. Optionally, the host cell can further contain a nucleic acid encoding a catalyst of disulfide bond formation.

Also within the scope of the invention are methods for producing a protein of interest (consisting of one or more polypeptides) having at least one disulfide bond. The method can comprise introducing into a host cell, e.g., as described above, a nucleic acid encoding the protein of interest, growing the host cells in conditions in which the protein is produced, and isolating the protein from the host cell. This method is applicable to produce any protein or polypeptide containing at least one disulfide bond. A person of skill in the art will, of course, recognize that the host cells of the invention can also be used for the production of proteins that do not contain any disulfide bonds. Proteins containing one or more disulfide bonds are usually secreted or membrane proteins. Thus, the method of the invention is useful for recombinantly producing growth or differentiation factors, receptors, secreted enzymes, as well as bacterial and viral proteins. Preferred proteins are those which have over 1, over 3, over 5, over 10, over 15 or even over 20 disulfide bonds.

The proteins and polypeptides, as well as compositions comprising such, are also part of the invention. Such proteins can be used for any purpose in which recombinant proteins are useful. For example, they can be used for diagnostic purposes (e.g., as binding agents, such as antibodies), for therapeutic purposes (e.g., tPA) or prophylactic purposes (e.g., as vaccines). In addition they can be used as food supplements, as well as components of wash powders, creams, etc.

BRIEF DESCRIPTION OF THE DRAWINGS

FIG. 1 is a schematic representation of the formation and isomerization of disulfide bonds (Rietsch and Beckwith (1998), infra).

FIG. 8A shows a portion of the nucleotide sequence and encoded amino acid sequence of *E. coli* ahpC gene (amino acids 33 to 48 of GenBank Accession No. BAA02485). The nucleotide sequence of the wild type aphC gene shown corresponds to SEQ ID NO: 8 and the encoded amino acid sequence corresponds to SEQ ID NO: 9. The nucleotide sequence of the mutated aphC gene shown corresponds to SEQ ID NO: 10 and the encoded amino acid sequence corresponds to SEQ ID NO: 11. The area of repeated TCT triplets is highlighted and the additional TCT triplet in AhpC* is framed.

FIG. 8B is an alignment of amino acid sequences of AhpC proteins from different microorganisms and from the human species (HUMAN_TPA). The numbers represent the amino acid position of the first amino acid shown in each protein. The sequences correspond, from top to bottom, to SEQ ID Nos: 12-20.

FIG. 11 is a diagram representing the reduction pathways present in a prokaryotic cell in which the gor and trxB genes are biologically inactive, and the role that is probably played by AhpCF in such cells.

DETAILED DESCRIPTION OF THE INVENTION

General

Figure 2:
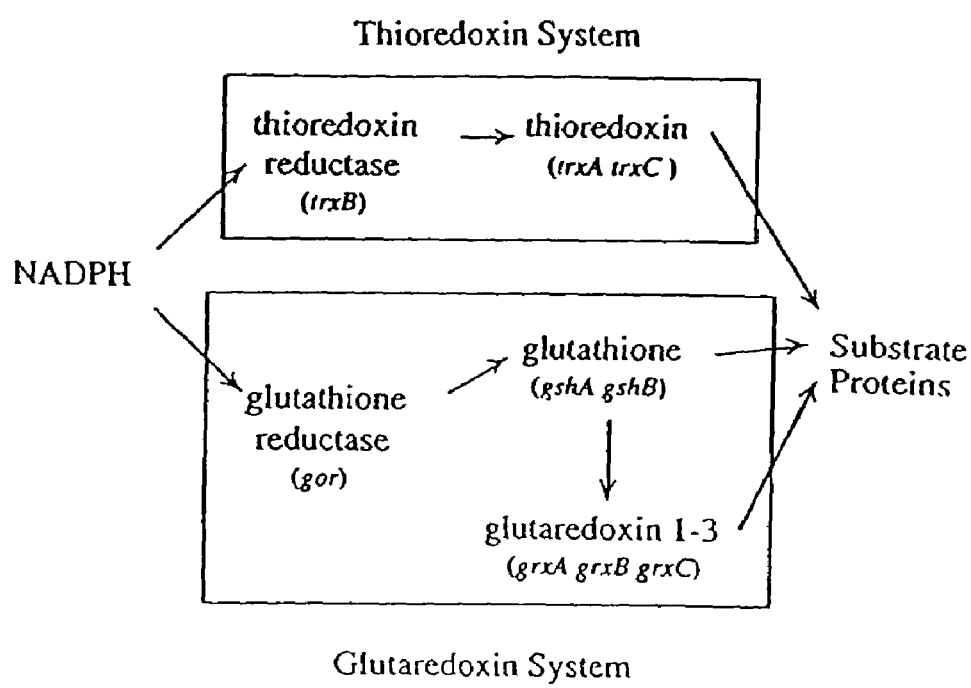
FIG. 2 is a schematic representation of the thioredoxin and glutaredoxin reducing systems in prokaryotic cells.

The invention pertains to compositions and methods for producing proteins which contain at least one disulfide bond (including any protein which, in its mature form does not have a disulfide bond, but a precursor of which contains a disulfide bond) in a host cell or host organism.

In a preferred embodiment, the invention includes modifying the cytoplasm of a host cell to favor proper folding of complex disulfide bond containing proteins, such as by shifting the redox status of the cytoplasm to a more oxidizing status. This host cell of the invention can then be used to express a protein of interest in the cytoplasm of the host cell. Although the invention pertains mostly to expression of proteins in the cytoplasm of host cells, a person of skill in the art will recognize that the techniques described herein can also be applied to other cellular compartments, e.g., the periplasm. Thus, the instant system provides, in particular, for the efficient production of mammalian proteins having at least one disulfide bond or which have at least one disulfide bond during their synthesis.

Host cells or organisms of the invention for the efficient production of disulfide bond containing proteins can be produced by various modifications or combinations of modifications of wild type cells or organisms or cells or organisms which have already been modified. In one embodiment, a host cell is modified by reducing or eliminating the level or activity of one or more reductase in the host cell. In a preferred embodiment, the reductase is selected from the group consisting of the thioredoxin reductase (trxB); glutathione (gshA and gshB); and the glutathione oxidoreductase (gor). Such a host cell can further be modified to increase its rate of growth, if necessary, such as selecting naturally occurring mutants, e.g., suppressor mutants, or by the introduction of a mutation or a heterologous DNA or stimulating the expression or activity of a gene, thereby resulting in an increased growth rate of the host cell. A modification of a host cell resulting in improved growth is referred to herein as "growth inducing modification." Growth of modified host cells can be improved or restored to that of wild type host cells by increasing the reducing environment of the cytoplasm, preferably without affecting the oxidative environment necessary for appropriate oxidation of disulfide bond containing proteins. Accordingly, the oxidizing role of the thioredoxins in the host cell is preferably not modified. In one embodiment, a modified host cell is modified by altering the activity of the AphC subunit of the alkyl hydroperoxidase AhpCF, such as by mutating the region of the aphC gene containing four TCT triplets, so that the enzyme has a new reducing activity. A preferred *E. coli* bacterial strain having a mutated aphC gene is the strain FA113 which has been deposited at the ATCC and has been assigned ATCC Accession No. PTA-939.

A host cell can further be modified by increasing the level or activity of a catalyst of disulfide bond formation and/or isomerization, such as by overexpressing or stimulating the activity of the DsbC protein or a variant of a thioredoxin (trx) or glutaredoxin (grx) or variant or homolog thereof. Thus, in one embodiment the invention provides a host cell, e.g., an *E. coli* cell, in which the thioredoxin reductase (trxB) and the glutathione oxidoreductase (gor) genes each contain a null mutation, and the host cell further contains a growth inducing modification, e.g., a mutation, improving its growth rate, and e.g., allowing it to grow at a rate similar to that of its wild type counterpart, such as the *E. coli* strain having ATCC Accession No. PTA-939 (FA113).

Another preferred embodiment provides an *E. coli* strain, having a null mutation in each of the thioredoxin reductase gene (trxB) and in a gene encoding a glutathione biosynthetic enzyme (gshA), and the cell further comprises a growth inducing modification, e.g., a mutation, allowing it to grow at essentially the same rate as the corresponding wild-type *E. coli* strain. A bacterial strain having this genotype has been deposited with the ATCC and has been assigned ATCC Accession No. PTA-938. The strains FA112 and FA113 cells are further described in the Examples. In another preferred embodiment, the invention provides an *E. coli* BL-21 trxB gor supp mutant.

In an even more preferred embodiment, a host cell further contains a plasmid encoding the DsbC protein (isomerase). In another embodiment, the host cell containing a null mutation in the thioredoxin reductase and the glutathione oxidoreductase genes, and optionally a growth inducing modification, further contains at least one plasmid encoding a mutant or variant of a thioredoxin or glutaredoxin gene.

In another embodiment, the invention provides a host cell comprising a null mutation in one or more of the thioredoxin reductase (trxB), a glutathione biosynthetic enzyme (gsha and gshB), and the glutathione oxidoreductase (gor) genes, contains one or more plasmids encoding one or more catalyst proteins, e.g., DsbC. The host cell may of may not contain a growth inducing modification, e.g., a mutation. Where the host cell does not have a growth inducing modificatin, such host cells may require the addition of an agent to their growth media, such as a reducing agent.

For purposes of convenience, a list of at least some prokaryotic proteins which are useful in the invention are set forth in Table 1.

TABLE 1

Thiol-disulfide oxidoreductases and their functions

| Gene Product | Gene Name | Location/Function | redox potential |
|---|---|---|---|
| Thioredoxin 1 | trxA | cytoplasmic reductant; reduces dsbC | −270 mV |
| Thioredoxin 2 | trxC | cytoplasmic reductant | |
| Thioredoxin reductase | trxB | Reduction of thioredoxins | |
| Glutaredoxin 1 | grxA | cytoplasmic reductant | −233 mV |
| Glutaredoxin 2 | grxB | cytoplasmic reductant | |
| Glutaredoxin 3 | grxA | cytoplasmic reductant | −198 mV |
| Glutathione oxidoreductase | gor | reduction of oxidized glutathione | |
| DsbA | dsbA | periplasmic protein, required for disulfide bond formation | −120 mV |
| DsbB | dsbB | cytoplasmic membrane protein; oxidation of DsbA | |
| DsbC | dsbC | periplasmic protein, required for disulfide bond isomerization | −130 mV |
| DsbD (DipZ) | dsbD (dipZ) | cytoplasmic membrane protein; reduction of DsbC | |
| DsbE (CcmG) | dsbE (ccmG) | cytoplasmic membrane protein, required for cytochrome c biogenesis | |
| DsbG | dsbG | periplasmic protein | |

(Rietsch and Beckwith (1998) Ann. Rev. Genet. 32: 163)

Other modifications or combinations of modifications of host cells are described infra. Although a person of skill in the art will readily be able to predict which modifications or combination of modifications would result in a host cell that is efficient in the production of disulfide containing proteins, various simple methods are available for confirming this (see, infra).

At least one advantage of synthesizing proteins in the cytoplasm of a host cell, as opposed to the periplasm, is that the kinetics of protein oxidation in the cytoplasm are slower than than those in the periplasm. For example, as shown in the Examples (FIG. 4), the half-life for the oxidation of alkaline phosphatase in the cytoplasm is well over a minute, whereas, the protein is nearly fully oxidized within fewer than 40 seconds in the periplasm. A slower oxidation rate is likely to be more favorable because in that case disulfide bond formation is more likely to be determined by the conformational preferences of the polypeptide chain which should result in the alignment of the proper cysteine residues. Second, the oxidation of proteins in the periplasm by DsbA, a protein required for disulfide bond formation which is naturally present only in the periplasm, may be detrimental for the folding of those proteins with multiple disulfides. DsbA is a very efficient enzyme; however, it tends to place disulfide bonds in polypeptides randomly with little regard for the native conformation. Random oxidation results in the formation of scrambled disulfides which can be difficult to rearrange. The addition of reduced glutathione to the medium, rendering the periplasmic space less oxidizing, increases the yield of eukaryotic disulfide-bonded proteins co-expressed in the periplasm of *E. coli* with DsbA or rat PDI (Wunderlich, et al. (1993) *J. Biol. Chem.* 268: 24547; Ostermeier, et al. (1996) *J. Biol. Chem.* 271: 10616). The implication is that somewhat more reducing conditions, than those naturally present in the periplasm, facilitate the folding of eukaryotic proteins containing multiple disulfide bonds. Such conditions can be found in the cytoplasm of cells, in particular prokaryotic cells.

Furthermore, although some proteins can be expressed in the bacterial periplasm at high levels (Joly et al. (1998) *PNAS* 95: 2773), often high level secretion, particularly of heterologous proteins, can interfere with the normal function of the Sec pathway causing cell toxicity. Even overexpression of homologous proteins can result in cell toxicity, as shown, e.g., in the overexpression of dsbC gene from a strong promoter in FIG. 4. Expression in the cytoplasm, together with, e.g., either signal sequenceless DsbC or "Grx-like" variant TrxA, circumvents this problem. Thus, not only can complex disulfide bonds be formed more readily in the cytoplasm, greater cell yields can be achieved as well.

Other aspects of the invention are described below or will be apparent to those skilled in the art in light of the present disclosure.

Definitions

For convenience, the meaning of certain terms and phrases employed in the specification, examples, and appended claims are provided below. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a mutation" includes two or more such mutations, and the like.

The term "oxidation-reduction potential," used interchangeably herein with "redox potential," of an active site disulfide bond reflects whether an enzyme is more reducing or oxidizing. In an oxidation-reduction reaction, the atom that increases in oxidation number (and thereby loses electrons) is said to undergo oxidation, or to be oxidized. The atom that is reduced in oxidation number (and thereby gains electrons) is said to undergo reduction, or be reduced. For example, the redox potential of the endoplasmic reticulumn has been estimated to be in the range of −172 to −188 mV (Rietsch and Beckwith (1998), infra), based on the ratio of reduced to oxidized glutathione. Table I lists the redox potential of various enzymes.

The term "standard state redox potential" or "$E^{o\prime}$" refers to a redox potential measured in standard conditions, e.g., in 1M concentration and at pH 7.0.

The term "oxidant" or "oxidizing agent" refers to a compound which oxidizes molecules in its environment, i.e., which changes the molecules in its environment to become more oxidized and more oxidizing. An oxidant acts by accepting electrons, thereby becoming itself reduced after having oxidized a substrate. Thus, an oxidant is an agent which accepts electrons.

The term "oxidizing conditions" or "oxidizing environment" refers to a condition or an environment in which a substrate is more likely to become oxidized than reduced. For example, the periplasm of a wild type bacteria constitutes an oxidizing environment, whereas the cytoplasm is a reducing environment.

When referring to an enzyme in an "oxidized state", it refers to the enzyme having less electrons than its reduced form.

The term "reductant" or "reducing agent" refers to a compound which reduces molecules in its environment, i.e., which changes molecules in its environment to become more reduced and more reducing. A reducing agent acts by donating electrons, thereby becoming itself oxidized after having reduced a substrate. Thus, a reducing agent is an agent which donates electrons. Examples of reducing agents include dithiothreitol (DTT), -mercaptoethanol, cysteine, thioglycolate, cysteamine, glutathione, and sodium borohydride.

The term "reductase" refers to a thioredoxin reductase, glutathione or glutathione reductase (also referred to as "cysteine oxido-reductases) or any other enzyme that can reduce members of the thioredoxin or glutaredoxin systems.

The term "reductase pathways" refers to the systems in cells which maintain the environment in reducing conditions, and includes the glutaredoxin system and the thioredoxin system (see FIG. 2).

The term "reducing conditions" or "reducing environment" refers to a condition or an environment in which a substrate is more likely to become reduced than oxidized. For example, the cytoplasm of a eukaryotic cell constitutes a reducing environment. The redox potential of the cytoplasm has been estimated to be −260-270 mV (see Hwang et al. (1992) *Science* 257: 1496).

"Disulfide bond formation" or "disulfide bond oxidation", used interchangeably herein, refers to the process of forming a covalent bond between two cysteines present in one or two polypeptides, which is schematized as "—S—S—" (see FIG. 1). Oxidation of disulfide bonds is mediated by thiol-disulfide exchange between the active site cysteines of enzymes and cysteines in the target protein (see FIG. 1). Disulfide bond formation is catalyzed by enzymes which are referred to as catalysts of disulfide bond formation.

When referring to an enzyme in a "reduced state", it refers to the enzyme having more electrons than its oxidized form.

"Disulfide bond reduction" refers to the process of cleaving a disulfide bond, thereby resulting in two thiol groups (—SH groups) (see FIG. 1). Reduction of disulfide bonds is mediated by thiol-disulfide exchange between the active site cysteines of enzymes and cysteines in the target protein (see FIG. 1).

The term "disulfide bond isomerization" refers to an exchange of disulfide bonds between different cysteines, i.e., the shuffling of disulfide bonds (see FIG. 1). Isomerization of disulfide bonds is mediated by thiol-disulfide exchange between the active site cysteines of enzymes and cysteines in the target protein (see FIG. 1) and catalyzed by isomeras. In *E. coli*, isomerization is catalyzed by DsbC, a periplasmic disulfide bond oxidoreductase.

"Protein disulfide bond isomerases" refer to proteins which catalyze the isomerization of disulfide bonds in proteins. Without wanting to be limited to a specific mechanism of action, isomerases are thought to act initially by invading incorrect disulfide bonds that have been formed in proteins and then allowing or promoting isomerization of the disulfide bond. To carry out this process, it is posited that the two cysteines in teh Cys-Xaa-Xaa-Cys motif must be in the reduced state (FIG. 1). In fact, DsbC is found with its inactive site cysteines in the reduced state in wild-type *E. coli*. DsbC is maintained in a reduced state in a cell by the cytoplasmic membrane protein DsbD (or DipZ protein).

A "catalyst of disulfide bond formation" is an agent which stimulates disulfide bond formation. Such an agent must be in an oxidized state to be active.

A "catalyst of disulfide bond isomerization", also referred to as an "disulfide bond isomerase" is an agent which stimulates disulfide bond isomerization. Such an agent must be in a reduced form to be active.

The term "thioredoxin superfamily" refers to the group of enzymes containing a "thioredoxin fold" which catalyze the reduction, formation, and/or isomerization of disulfide bonds and exert their activity through a redox active disulfide in a Cys-Xaa1-Xaa2-Cys (SEQ ID NO: 1) motif, and includes the thioredoxins, glutaredoxins, DsbA, DsbD, and DsbC.

The term "thioredoxin fold" refers to an overall protein structural motif that is shared by the members of the thioredoxin superfamily. Thus, although thioredoxins and glutaredoxins may have relatively different amino acid sequences, they share a similar secondary structure, i.e., a similar overall fold, referred to as the thioredoxin fold. The thioredoxin fold consists of a central four-stranded beta-sheet flanked by three alpha-helices in the order (see, e.g., FIG. 1 in Jordan et al. (1997), *J. Bio. Chem.* 272:18044). The thioredoxin fold has been found in five distinct classes of proteins that have the common property of interacting with cysteine-containing substrates (see, e.g., Martin J. L. (1995) *Structure* 3: 245 and Aslund et al. (1996) *J. Biol. Chem.* 271:6736).

The term "thioredoxin family" includes thioredoxin 1 (trxA), thioredoxin 2 (trxC), and thioredoxin reductase (trxB), as described in Rietsch and Beckwith (1998) *Ann. Rev. Genet.* 32: 163.

The term "thioredoxin" includes thioredoxin 1 (trxA) and thioredoxin 2 (trxC), as described in Rietsch and Beckwith (1998) *Ann. Rev. Genet.* 32: 163. Thioredoxins are small proteins characterized by the presence of the motif Cys-Xaa-Xaa-Cys (where Xaa denotes any amino acid) in their active site. Thioredoxin is re-reduced by thioredoxin reductase (encoded by trxB gene) and NADPH (see FIG. 2). In a trxB mutant, thioredoxin accumulates in an oxidized form.

The term "glutaredoxin family" includes glutaredoxin 1 (grxA), glutaredoxin 2 (grxB), glutaredoxin 3 (grxC), and glutathione oxidoreductase (gor), as described in Rietsch and Beckwith (1998) *Ann. Rev. Genet.* 32: 163.

The term "glutaredoxin" includes glutaredoxin 1 (grxA), glutaredoxin 2 (grxB), and glutaredoxin 3 (grxC), as described in Rietsch and Beckwith (1998) *Ann. Rev. Genet.* 32: 163. Glutaredoxins (encoded by genes termed "grx", such as grxA, grxB, and grxC genes) which contain the Cys-Xaa-Xaa-Cys (SEQ ID NO: 1) (Xaa being any amino acid) active site motif, but are distinct from thioredoxins in that they are not reduced by thioredoxin reductase, but by the small tripeptide glutathione, which itself is reduced by glutathione oxidoreductase (encoded by the gor gene) in the presence of NADPH (see FIG. 2).

The terms "gshA gene" and "gshB gene" refer to the genes encoding glutathione biosynthetic enzymes.

The term "gor gene" refers to the glutathione oxidoreductase gene.

When referring to a protein, the first letter of the name of the protein is generally a capital letter. When referred to a gene, the first letter of the name of the gene is generally a small cap, and may be, optionally, spelled in italics.

"DsbC", is a protein encoded by the gene dsbC, which catalyzes disulfide bond isomerization. Certain proteins require DsbC for their folding in vivo, e.g., mouse urokinase, bovine pancreatic trypsin inhibitor (BPTI), insulin like growth factor-1, and melanocyte growth stimulating activity (MGSA) (see Rietsch and Beckwith (1998) *Ann. Rev. Genet.* 32: 163, and references cited therein). DsbC null mutants have a defect in the folding of proteins with multiple disulfide bonds.

"DsbD", also referred to as "DipZ", is encoded by the gene dsbD also referred to as dipZ gene, and is a cytoplasmic membrane protein that maintains DsbC in a reduced state, i.e., in an active state. DsbD null mutants have a defect in the folding of proteins with multiple disulfide bonds and causes DsbC to accumulate in an oxidized form, i.e., inactive form.

"DsbB," which is encoded by the gene dsbB, is a cytoplasmic protein which oxidizes DsbA. DsbB contains a Cys-Xaa-Xaa-Cys (SEQ ID NO: 1) (Xaa being any amino acid residue) motif. DsbB may be oxidized by passing electrons to the restpiratory chain.

"DsbA" is a periplasmic protein required for disulfide bond formation that is encoded by the gene dsbA.

The term "protein" refers to a single polypeptide or to a complex comprising at least two (two or more) polypeptides or polypeptidic chains which can be connected by one or more disulfide bond(s).

A "host organism" is intended to encompass a multicellular as well as a unicellular organism. A unicellular host organism is used interchangeably with a "host cell".

A "host cell" is any cell that can be used for the purposes of this invention.

When referring to a "modification of host cells," the term "modification" includes a transient or a permanent alteration of the host cell, e.g., a constitutive or an inducible alteration. A modification can be a genetic alteration.

A "growth inducing modification" of a host cells refers to a modification of a host cell resulting in improved or faster growth of the host cell. The modification can restore the growth rate of the cell to that of a corresponding wild type host cell, or it can merely improve it. Growth rate of host cells can be determined by counting the cells at different time points, and in the case of prokaryotic host cells, e.g., by measuring the optical density of a culture (e.g., at about 600 nm) at different time points. A modification can be a mutation of a gene of the host cell, e.g., a mutation in AphC called AhpC*, or it can be the introduction of a gene into the host cell, e.g., introduction of a gene encoding AphC*.

As used herein, "signal sequence" or "signal polypeptide" refers to a peptide that directs a polypeptide to be secreted by a cell, to become membrane bound or to be secreted into the periplasm of a prokaryotice cell. To assure that a polypepeptide is maintained in the cytoplasm of a cell, the signal peptide is removed. Signal peptides have common characteristics, including hydrophobicity, that allows them to be identified.

An "over-expressed" gene product is one that is expressed at levels greater than normal endogenous expression for that gene product. It can be accomplished, e.g., by introducing a recombinant construction that directs expression of a gene product into a host cell, or by altering basal levels of expression of an endogenous gene product, e.g., by inducing its transcription.

"Inducible" promoters are promoters which direct transcription at an increased or decreased rate upon binding of a transcription factor or an inducer. "Transcription factors" as used herein include any factors that can bind to a regulatory or control region of a promoter and thereby effect transcription. The synthesis or the promoter binding ability of a transcription factor within the host cell can be controlled by exposing the host to an "inducer" or removing an inducer from the host cell medium. Accordingly, to regulate expression of an inducible promoter, an inducer is added or removed from the growth medium of the host cell.

As used herein, the phrase "to induce expression" means to increase the amount of transcription from specific genes by exposure of the cells containing such genes to an effector or inducer.

An "inducer" is a chemical or physical agent which, when given to a population of cells, will increase the amount of transcription from specific genes. These are usually small molecules whose effects are specific to particular operons or groups of genes, and can include sugars, phosphate, alcohol, metal ions, hormones, heat, cold, and the like. For example, isopropylthio-beta-galactoside (IPTG) and lactose are inducers of the tacII promoter, and L-arabinose is a suitable inducer of the arabinose promoter. The pho gene promoter, such as phoA and pho5, is inducible by low phosphate concentrations in the medium.

As used herein, a "protein or polypeptide of interest" refers generally to a protein or polypeptide which can be expressed in the host cell and recovered from the host cell. Preferably such a polypeptide comprises at least about 5 amino acids, preferably at least about 10 amino acids, 15 amino acids, 20 amino acids, 25, 30, 35, 40, 50, 100 amino acids or more than 120 amino acids.

The term "containing at least one disulfide bond" when referring to a protein or polypeptide refers to a protein or polypeptide which has a disulfide bond in its mature form and/or in a precursor form.

A "heterologous protein or polypeptide" refers to a protein or polypeptide which is not normally produced in the host cell. A heterologous polypeptide can be from the same species and type as the host cell provide that it is expressed from a nucleic acid which has been introduced into the host cell.

The phrase "hydrophobic residues" refers to the residues norleucine, cysteine, methionine, alanine, valine, leucine, tyrosine, phenylalanine, tryptophan, and isoleucine.

The expression "control sequences" refers to DNA sequences necessary for the expression of an operably linked coding sequence in a particular host organism. The control sequences that are suitable for bacteria include a promoter such as the alkaline phosphatase promoter, optionally an operator sequence, and a ribosome-binding site.

A nucleic acid is "operably linked" to another nucleic acid when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Production phase of cell growth" refers to the period of time during cell growth following induction of the promoter when the polypeptide of interest is being produced.

"Plasmids" for use in the invention include those which become integrated into the host cell genome and those which are autonomously replicating plasmids.

The "Km" of an enzyme refers to the Michaelis constant of the enzyme which is equal to the substrate concentration at which the reaction rate is half its maximal value (Vmax). The Km of an enzyme can be determined by methods known in the art. Typical Km values range from $10^{-1}$ to $10^{-6}$ M.

The term "k" or "Kcal" refers to the rate constant in an enzymatic reaction.

Figure 9:
FIG. 9 is a diagam showing the two different forms of AhpC that can be found in a cell depending on the oxidative stress-inducing signal. The form on the left represents the wil-dtype enzyme and the form on the right, the mutant enzyme.

The term "AhpCF" refers to the alkyl hydrogen peroxide reductase, also referred to herein as alkyl hydroperoxide reductase which comprises two subunits (see FIG. 9). AhpC is the smaller subunit and the other subunit is the flavoenzyme AhpF (Tarataglia et al, J. Biol. Chem., Volume 265, 10535-10540, 1990; Smillie et al, Genbank submission NCBL gi; 216542, 1993). This enzymatic complex (or system) scavenges oxygen and its derivatives. The AhpC protein contains the peroxide reducing catalytic site, which is centered around amino acid 47 (cysteine) in the *E. coli* enzyme (SEQ ID NO: 22), and the ahpF protein is an NAD(P)H dehydrogenase. Oxygen stress responses involving AhpC homologs are highly conserved in bacteria, yeast, parasites and even in vertebrates (Chae et al, J. Biol. Chem., Volume 269, 27670-27678, 1994; Tsuji et al, Biochem. J., Volume 307, 377-381, 1995; Armstrong-Buisseret et al, Microbiology-UK, Volume 141, 1655-1661, 1995; Bruchhaus et al, Molecular and Biochemical Parasitology, Volume 70, 187-191, 1995; Ferrante et al, PNAS, USA, Volume 92, 7617-7621, 1995; Wilson et al, Mol. Microbiol., Volume 19, 1025-1034, 1996; and FIG. 8B).

Host Cells and Organisms of the Invention

The invention generally is applicable to any host organism of host cell which is capable of expressing heterologous polypeptides, and which can preferably be genetically engineered. A host organism is preferably a unicellular host organism, however, multicellular organisms are also encompassed in the invention, provided the organism can be modified as described herein and a polypeptide of interest expressed therein. For purposes of clarity, the term "host cell" will be used herein throughout, but it should be understood, that a host organism can be substituted for the host cell, unless unfeasable for technical reasons. In a preferred embodiment the host cell is a prokaryotic cell. In another embodiment, the host cell is a eukaryotic cell, such as a yeast cell or a mammalian cell. In an even more preferred embodiment, the host cell is a bacterial cell, preferably a gram negative bacterial cell, e.g., an *E. coli* bacteria.

The host organisms can be aerobic or anaerobic organisms.

Preferred host cells are those which have characteristics which are favorable for expressing polypeptides, such as host cells having fewer proteases than other types of cells. Thus, for example, host cells which have been modified to reduce the level or activity of proteases can be used, e.g., BL-21 (see below).

Other preferred bacterial strains have been modified to become lysogenic for the T7 (DE3) phage, allowing for expression of proteins using the pET series of plasmids.

Suitable bacteria for this purpose include archaebacteria and eubacteria, especially *eubacteria*, and most preferably *Enterobacteriaceae*. Other examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla,* and *Paracoccus*. Suitable *E. coli* hosts include *E. coli* DHB4, *E. coli* BL-21 (which are deficient in both lon (Phillips et al. (1984) *J. Bacteriol.* 159: 283.) and ompT proteases), *E. coli* AD494, *E. coli* W3110 (ATCC 27,325), *E. coli* 294 (ATCC 31,446), *E. coli* B, and *E. coli* X1776 (ATCC 31,537). Other strains include *E. coli* B834 which are methionine deficient and, therefore, enables high specific activity labeling of target proteins with $^{35}$S-methionine or selenomethionine (Leahy et al. (1992) *Science* 258, 987). Yet other strains of interest include the BLR strain, and the K-12 strains HMS174 and NovaBlue, which are recA-derivative that improve plasmid monomer yields and may help stabilize target plasmids containing repetitive sequences (these strains can be obtained from Novagen).

These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

*E. coli* strain W3110 is also a preferred host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 1A2, which has the complete genotype tonA DELTA (also known as DELTA fhuA); *E. coli* W3110 strain 9E4, which has the complete genotype tonA DELTA ptr3; *E. coli* W3110 strain 27C7 (ATCC 55,244), which has the complete genotype tonA DELTA ptr3 phoA DELTA E15 DELTA (argF-lac)169 ompT DELTA degP41kan$^R$; *E. coli* W3110 strain 37D6, which has the complete genotype tonA DELTA ptr3 phoA DELTA E15 DELTA (argF-lac)169 ompT DELTA degP41kan$^R$ rbs7 DELTA ilvG; *E. coli* W3110 strain 40B4, which is strain 37D6 with a non-kanamycin resistant degP deletion mutation; *E. coli* W3110 strain 33D3, which has the complete genotype tonA ptr3 lacIq LacL8 ompT degP kan$^R$; *E. coli* W3110 strain 36F8, which has the complete genotype tonA phoA DELTA (argF-lac) ptr3 degP kan$^R$ ilvG$^+$, and is temperature resistant at 37° C.

The host cells of the invention can be stored, e.g., as glycerol stocks, which can be prepared according to known methods of the invention.

Modification of Host Cells to Favor Disulfide Bond Formation in their Cytoplasm

In one embodiment the invention provides a host cell having a cytoplasm that favors disulfide bond formation in proteins. Since normally the cytoplasm of a cell is composed of an essentially reducing environment, which disfavors disulfide bond formation, the host cell is, e.g., modified to shift the redox state of its cytoplasm to more oxidizing conditions. This can be achieved, e.g., by altering one or more reductase pathways in the host cell. Thus, in an illustrative embodiment, the invention comprises modifying one or more of the following two reductase systems existing, in particular, in prokaryotic cells: the thioredoxin/thioredoxin reductase pathway (the "thioredoxin system") and the glutathione/glutaredoxin pathway (the "glutaredoxin system"; see FIG. 2). The thioredoxin system consists of the thioredoxin reductase enzyme (TrxB) which reduces a thioredoxin (TrxA or TrxC) which then reduce substrate proteins. The glutaredoxin system consists of the glutathione reductase (also referred to as "glutathione oxidoreductase"; Gor) which reduces glutathione (GshA and GshB) which reduces a glutaredoxin (GrxA, GrxB, or GrxC) which then reduces substrate proteins (see, e.g., Rietsch and Beckwith (1998) *Ann. Rev. Genet.* 32: 163).

In a preferred embodiment of the invention, the cytoplasmic redox status of the cytoplasm of a host cell is increased (i.e., the redox status of the cytoplasm becomes a more oxidizing environment) by inhibiting or decreasing the activity or level of a reductase, such as the thioredoxin reductase (trxB), glutathione (gshA or gshB), or glutathione reductase (gor). In a preferred embodiment, expression of the reductase is eliminated, i.e., reduced to zero or to undetectable levels, by inactivating the gene encoding the reductase according to methods well known in the art and further set forth below. Thus, preferred host cells are completely devoid of the expression of a reductase, such as the thioredoxin reductase, glutathione, or the glutathione reductase. In another embodiment, expression of a reductase is inducible, i.e., it is expressed only in the presence or absence of a certain inducer. For example, a reductase can be expressed under the control of an arabinose promoter (further described herein). Accordingly, the reductase will be expressed only in the presence of arabinose, and not in its absence. A null phenotype is then created by cultivating the host cells in the absence of arabinose. Such a system also allows the control of the amount of reductase that is made in the host cell. When using an inducible reductase gene, it may be desirable to use a host cell which is devoid of the wild type reductase gene (see Examples).

In yet another embodiment the expression of a reductase in a host cell is reduced by inhibiting the transcription of the gene encoding the reductase, by degrading the RNA encoding the reductase, or by inhibiting translation of the RNA. Transcription and translation can be inhibited by introducing into, or expressing antisense nucleic acids in the host cell. Alternatively, these processes can be inhibited by contacting the host cells with small organic molecules which interfere with these processes. Such compounds can be identified, e.g., in screening assays. It will be understood that the expression of a reductase in a host cell can also be reduced or eliminated by modulating the expression of one or more proteins that control the expression of the reductase in the host cell by acting upstream of the reductase gene in its regulation. For example, expression of a reductase can be decreased by reducing the expression or activity of a factor that is necessary for the expression of the reductase.

Instead of, or in addition to, inhibiting or decreasing the level of the reductase protein in a host cell, the activity of, the reductase can be reduced or eliminated. In a particular embodiment, the host cell is incubated with a compound that inhibits the activity of a reductase, e.g., the thioredoxin reductase, glutathione, or the glutathione reductase. Such compounds can be identified in screening assays, by methods known in the art.

Alternatively, reductase expression can be prevented by the use of constructs that would allow the turning on of a protease to degrade the reductase. This can be done, e.g., by inserting a protease sensitive site in the reductase (see, e.g., Ehrman et al. (1997) *PNAS* 94:13111)

Preferred host cells of the invention fail to express, or have decreased expression or activity of the thioredoxin reductase (trxB) and one or more of the glutathione (gshA or gshB) and glutathione reductase (gor). Accordingly, a preferred host cell of the invention is a prokaryotic cell having a null mutation in trxB and a null mutation in gshA or in gor. As previously described, such double mutants may grow poorly, and it may be necessary to add a reductant, such as DTT, to their culture medium. In an illustrative example, an amount of DTT ranging from about 1 to 10 mM, preferably from about 2 to 4 mM, is appropriate to increase the growth of these cells. When a trxB gor or trxB gshA strain is grown in medium containing DTT and then transferred to medium lacking DTT, the cytoplasm becomes even more oxidizing than in the trxB strain, resulting in the accumulation of high levels of alkaline phosphatase or mouse urokinase activity (Prinz, et al. (1997) *J. Biol. Chem.* 272: 15661).

In conditions in which one does not desire to add DTT in the culture medium, one can use any of the above-described host cells in which the expression of one or more reductase genes is inducible. Alternatively, the host cells may be modified by the introduction of a growth inducing modification, e.g., by introducing a mutation (see below).

Gram positive prokaryotic cells, e.g., *Bacillus*, are known not to possess the glutaredoxin system. Thus, the redox status of the cytoplasm is reduced simply by reducing or eliminating the expression or activity of the reductase of the thioredoxin system. If the elimination of a reductase is lethal to the host cells, it may be necessary to render expression of the reductase inducible, such as by methods further described herein.

Modification of Host Cells to Obtain Favorable Growth

As set forth above, modification of a host cell that results in improved disulfide bond formation in the cytoplasm, such as by changing the redox potential of its cytoplasm, in particular, where the cytoplasm is rendered more oxidizing, the growth and survival of the cell may be affected. For example, a bacteria having a null mutation in the thioredoxin reductase gene and a null mutation in either of a glutathione gene or the glutathione reductase gene grows much more poorly than its wild type counterpart or even a single mutant having only one of these null mutations. As described in the Examples, growth of such cells can be improved by the addition in the growth medium of a reductant, such as DTT.

Alternatively, the growth of cells can be rescued by the selection of suppressor mutants, such as described in the Examples. In an illustrative embodiment, suppressor mutants are selected by growing cells in the presence of DTT for a certain time period, removing DTT from the culture media, and selecting fast growing colonies. For example, cells can be grown for 24 hours in the presence of 6 mM DTT. Fast growing cells can the isolated and diluted suspensions of these cells can then be plated to isolate single colonies. The growth rate of bacteria can be determined according to methods well known in the art.

Suppressor mutants can have mutations in any gene that compensates for the lack of growth due to null mutations in reductases. The mutation may be a loss of function mutation or a gain of function mutation. It is not necessary to know in which gene the suppressor mutation occurred in order to practice the invention. However, it might be of interest to know the identity of the mutation for increasing the growth rate of other strains of host cells without having to select for suppressor mutants, but simply by creating the same mutation as that in the suppressor mutant.

Several methods exist for determining the identity of the suppressor gene. For example, transposons can be mapped by linkage analysis, as described, e.g., in Kleckner et al. (1991) *Meth. Enzym.* 204:139. Alternatively, suppressor mutants can be obtained by random insertion of DNA into the host cell chromosome and sequencing the DNA of the host cell that is flanking the DNA inserted into the genome of the host cell, using primers which bind to the DNA insert. Such techniques are well known in the field of prokaryotic genetics.

The rapid growth of a trxB gor supp strain (FA113, see Examples) indicates that bacteria can tolerate large perturbations in their cytoplasmic thiol-disulfide redox potential. This implies that the vast majority of native cytoplasmic proteins in FA113 are unable to form aberrant disulfides, even under oxidizing conditions. Thus, suppressor mutations are likely to be capable of saving any host cell engineered as described herein from slow growth. More generally, suppressor mutations can be introduced into a strain to cure any type of defect or change a characteristic of a cell, in addition to increasing its growth rate.

As described in the Examples, the suppressor mutation in strain FA113 has been localized to the gene ahpC, encoding the small catalytic subunit of the alkyl hydroperoxidase, AhpCF, which catalyses the destruction of oxidative species, e.g., peroxidase. The mutation corresponds to the addition of a triplet within the region of the gene containing four TCT triplets (see FIG. 8A), which is a region which contains the cysteine (amino acid 47) that is located in the catalytic site of the enzyme. A nucleic acid encoding this mutated form of AhpC is set forth in SEQ ID NO: 23, and the amino acid encoded therefrom is set forth in SEQ ID NO: 24. The wild type nucleic acid and amino acids of AhpC are set forth in SEQ ID NO: 21 and 22, respectively, and correspond to GenBank Accessions Nos. D13187 (Feb. 3, 1998) and BAA02485 (Feb. 3, 1998), respectively. As further described in the Examples, this mutation essentially destroys the peroxidase activity of the enzyme. As further shown herein, the presence of mutated AhpC (referred to as AhpC*) provides growth enhancing capability to host cells only in the presence of AhpF and of a functional glutaredoxin system. Thus, it is likely that AhpC* enhances growth by reducing oxidized glutaredoxin 1 or glutathione. Generally, it is believed that the AhpC* increases the reducing capacity to the cytoplasm sufficient to allow growth.

Accordingly, growth of host cells can also be improved by introducing a modification in the host cell which increases the reducing capacity of its cytoplasm. The modification can be a mutation in a gene of the host cell, e.g., a mutation which increases the reducing potential of an enzyme, or which reduces the oxidizing potential of an enzyme. A preferred modification is a mutation in the AphC gene, e.g., a mutation in its catalytic domain. An even more preferred mutation is one that occurs in the TCT triplet repeat, such as the insertion of a TCT triplet, as shown in FIG. 8A. A preferred mutant AhpC has the amino acid sequence set forth in SEQ ID NO: 24. Other mutations can also be made to AhpC, provided that the mutation improves the growth of the cells. Identification of other mutations, e.g., in AhpC, that have a growth improving activity can be identified, e.g., by introducing random mutations in a host cell, e.g., one having mutations in trxB and in gor, and selecting for those having enhanced growth. The mere culture of such mutated cells will result in an enriched population of cells having growth inducing mutations, which can then be identified. Random mutations can be introduced and identified according to methods well known in the art of prokaryotic genetics.

As opposed to introducing a mutation in a particular gene to induce growth, one may also downregulate the expression of the gene by any of a variety of methods, including antisense expression or the contacting the cell with an agent that reduces transcription of the gene.

Alternatively, the modification of host cells can be the introduction into the host cell of a gene which enhances growth or stimulating the expression of a gene enhancing growth in the host cell. For example, a host cell can be modified by the introduction into the cell of a gene encoding a protein which increases the reducing capacity of the cytoplasm. In a preferred embodiment, the gene is a reductase. In an even more preferred embodiment, the gene encodes AhpC*. The gene can be maintained episomally or the gene can be integrated into the chromosome. It may be desirable, in certain circumstances to reduce or elimate the amount of the corresponding protein of the growth inducing gene. In the case in which a gene encoding AhpC* is introduced into a cell, and optionally overexpressed, it is not necessary to reduce expression of the wild type gene encoding AhpC, since it has been shown herein that AhpC* is dominant.

In view of the strong conservation of the AhpC genes across species (see, e.g., FIG. 8B), host cells other than E. coli can be modified in a similar fashion to improve their growth potential. For example, a host cell can be modified by introducing a gene encoding a mutated AhpC protein, such as one having a mutation in the repeated triplet region.

It is likely that the reason the trxB,gor and trxB,gshA strains do not grow is that they do not have sufficient reducing power to maintain the essential enzyme ribonucleotide reductase in the reduced, active state. Accordingly, another class of suppressors that may restore growth to these strains is one in which one (or more) of the several ribonucleotide reductase genes on the E. coli chromosome is altered by mutation so that it no longer needs the thioredoxin or glutathione/glutaredoxin pathways as a source of reducing power. It would obtain its electrons from one of the other possible sources in the cytoplasm. Such suppressor strains may, in addition, be even more efficient at disulfide bond formation than the strains having a mutation in ahpC because, in contrast to the likely consequence of the ahpC mutation, these suppressor mutations do not generate any new reducing power. The cytoplasm may well be more oxidizing vis-a-vis disulfide bonds than FA113.

Modification of Host Cells by the Addition of Genes Encoding Catalysts of Disulfide Bond Formation and/or Isomerization As shown in the Examples, proper folding of polypeptides comprising numerous disulfide bonds expressed in host cells was increased by cotransformation of the host cell with a catalyst of disulfide bond formation and/or a catalyst of disulfide bond isomerization. Thus, generally the invention provides host cells which are modified to over-express or increase the activity of one or more catalyst(s) of disulfide bond formation and/or isomerization.

In a preferred embodiment, a catalyst of disulfide bond formation is an enzyme which facilitates, or increases the speed of, disulfide bond formation. Generally, a catalyst of disulfide bond formation will have the following characteristics: it is able to accumulate in oxidized form in the cytoplasm, and the oxidized form of the protein catalyst is efficient at transferring its disulfide to a substrate protein. Accordingly, since a catalyst of disulfide bond formation must be in oxidized form in the cytoplasm to be active, the catalyst will generally have a low redox potential, e.g., in the range of the redox potential of the thioredoxins and glutaredoxins. Thus, catalysts of disulfide bond formation will preferably have a redox potential of at most about −270 mV, preferably at most about −260 mV, at most about −250 mV, at most about −240 mV, at most about −230 mV, at most about −220 mV, at most about −210 mV, at most about −200 mV, or at most about −190 mV. Other preferred catalysts have a redox potential in the range of about −260 to −190 mV, more preferably, of about −230 to −190 mV, and even more preferably of about −210 to −190 mV. However, catalysts of disulfide bond formation can also have a redox potential outside of these ranges, provided that the enzyme is capable of catalyzing disulfide bond formation, as can be shown in in vitro or in vivo assays, as further set forth herein.

Catalysts of disulfide bond isomerization are enzymes which are capable to form disulfide bonds, but which are also capable of shuffling disulfide bonds. Generally, catalysts of disulfide bond isomerization will be in a reduced state in the cytolasm, so that they are capable of invading incorrectly formed disulfide bonds. Accordingly, an isomerase will generally have a higher redox potential than a catalyst of disulfide bond formation. Preferred isomerases have a redox potential of at most about −200 mV, at most about −190 mV, at most about −180 mV, preferably at most about −170 mV, preferably at most about −160 mV, and most preferably at most about −150 mV. However, an isomerase can also have a redox potential outside of these ranges, provided that the enzyme is capable of catalyzing isomerization of disulfide bonds, which can be demonstrated in vitro or in vivo, as further set forth hererin.

A preferred catalyst of disulfide bond isomerization of the invention is DsbC or an variant of homolog thereof. Thus, a host cell of the invention, such as a host cell in which the activity or level of expression of a reductase enzyme is decreased or eliminated, can be transformed with a gene encoding DsbC. As further described in the Examples, co-expression of DsbC (having a redox potential of −130 mV) in a host cell resulted in a dramatic increase in the production of disulfide bond containing proteins.

In an illustrative embodiment, the gene encoding DsbC is constitutively expressed, i.e., under the control of a constitutive promoter. Alternatively, the gene can be inducible, i.e., under the control of an inducible promoter. In the later situation, DsbC can the be induced, e.g., upon the addition to the culture medium of the inducer. Inducible promoters are further described herein.

Generally, where the catalyst of the invention is a protein which is normally expressed in the periplasm or is secreted, expression of the catalyst in the cytoplasm of the host cell requires that the signal sequence be deleted.

Other preferred catalysts of the invention are proteins or compounds which regulate the expression or activity of a catalyst, e.g., DsbC. For example, disulfide bond formation can be stimulated in a host cell by overexpressing the cytoplasmic membrane protein DsbD (DipZ), which reduces DsbC, and thereby augments DsbC's activity to function as an isomerase. Alternatively, the activity of DsbD can be increased, e.g., by inducing its reduction.

Another catalyst that can be used in certain circumstances include the protein DsbA, which increases disulfide bond formation. DsbA has been shown in vitro to be an extremely efficient catalyst of disulfide bond formation (see Rietsch and Beckwith (1998) infra). This property is consistent with the high redox potential of its active site disulfide bond. DsbA oxidizes its substrates by transferring the disulfide bond from its active site to the target protein. Overexpression of this protein, or stimulation of its activity, is preferably used for expressing proteins containing a low number of disulfide bonds, e.g., a single disulfide bond, rather than proteins containing high number of disulfide bonds. It has, in fact, been reported that DsbA promotes the formation of incorrect disulfide bonds in substrate proteins containing multiple disulfide bonds. Thus, when expressing complicated proteins in a host cell which overexpresses DsbA or in which its activity is stimulated, it may be desirable to overexpress or stimulate the activity of a disulfide bond isomerase, e.g., the isomerase DsbC.

The activity of DsbA can be stimulated by overexpressing or stimulating the activity of an enzyme which oxidizes DsbA. Indeed, after catalyzing disulfide bond formation, DsbA is left in a reduced state, and the active site disulfide bond must be reoxidized in order for DsbA to catalyze another round of disulfide bond formation. Reoxidation of DsbA is performed by the integral membrane protein DsbB. Thus, activation of DsbA can be done by overexpressing, or stimulating the activity of, the protein DsbB.

In yet another embodiment, the activity or level of thioredoxins or glutaredoxins is increased in the host cell. It has been shown that thioredoxins, which under normal, i.e., wild type cytoplasmic conditions act as potent reductases, can in fact act as oxidants when present in oxidizing conditions, such as in a cytoplasm in which the expression of one or more of the reductases thioredoxin reductase, glutathione, and glutathione reductase is inhibited (Stewart et al. (1998) *EMBO J.* 17:5543). Also, as described in the Examples, co-expression of wild type thioredoxin (−270 mV) increased disulfide bond formation. Thus, these proteins will stimulate disulfide bond formation in host cells which fail to express wild type amounts of one or more reductase. Accordingly, overexpression of one or more of thioredoxins or glutaredoxins will increase the production of correctly folded proteins comprising at least one disulfide bond.

Although wild-type thioredoxin and glutaredoxin enzymes can be used as catalysts in the methods of the invention, preferred catalysts include mutant versions of these enzymes that are more effective at promoting disulfide bond formation and/or isomerization than their wild type counterparts. For example, a variant of thioredoxin (trxA), that is more oxidizing than its wildtype counterpart, can be expressed in a host cell. As described further herein, the redox potential of most cysteine oxidoreductases, including TrxA, is strongly influenced by the sequence of the dipeptide within the C-Xaa-Xaa-C (SEQ ID NO: 1) active site motif (Mossner, et al. (1999) *J. Biol. Chem.* 274: 25254; Mossner, et al. (1998) *Protein Sci.* 7: 1233; Grauschopf, et al. (1995) *Cell* 83: 947). As shown in the Examples, co-expression of more oxidizing TrxA variants (higher redox potential) resulted in higher expression of the disulfide bond containing proteins. Indeed, the efficiency of disulfide bond formation was markedly increased by introducing plasmids expressing thioredoxin mutant proteins poised at a higher redox potential, than their wild type counterparts. Preferred thioredoxin or glutaredoxin variants include those that are mutated in the active site of the enzyme, i.e., in the C-Xaa-Xaa-C (SEQ ID NO: 1) sequence. The variant can have an amino acid substitution, deletion or addition. Preferred variants include -CGSC- (SEQ ID NO: 3); -CPYC- (SEQ ID NO: 4), which is the active site found in wild type Grx proteins, and which is referred to herein as the "Grx-like" variant; --CPHC- (SEQ ID NO: 5), which is the active site found in the wild type DsbA protein, and which is referred to herein as the "DsbA-like" variant; and -CGHC- (SEQ ID NO: 6), which is the active site found in the wild type rat protein disulfide isomerase (PDI) and which is referred to herein as the "PDI-like" thioredoxin mutant. The redox potential of these mutants have been estimated from the equilibrium constants with glutathione solutions to be −195 mV, −204 mV and −221 mV, respectively, i.e., higher than the −270 mV of the wild type thioredoxin (Mossner et al. (1998) *Protein Sci.* 7:1233).

Without wanting to be limited to a specific mechanism of action, it is believed that the variants of thioredoxin are more potent catalysts than the wildtype counterpart, since their redox potential are higher than that of the wildtype thioredoxin (−270 mV). This difference in redox potential likely results in wild type thioredoxin being fully oxidized, as it has been observed, whereas the higher redox potential variants were found to accumulate predominantly in reduced form, which can then serve as a catalyst for disulfide bond isomerization.

Accordingly, preferred thioredoxin or glutaredoxin variants for use as catalysts in the invention comprise a redox potential of at most about −270 mV, preferably at most about −260 mV, at most about −250 mV, at most about −240 mV, at most about −230 mV, at most about −220 mV, at most about −210 mV, at most about −200 mV, or at most about −190 mV. Other preferred catalysts have a redox potential in the range of about −260 to −190 mV, more preferably, of about −230 to −190 mV, and even more preferably of about −210 to −190 mV. However, a variant can also have a redox potential outside of these ranges, provided that the variant is capable of catalyzing isomerization of disulfide bonds, which can be demonstrated in vitro or in vivo, as further set forth herein.

The redox potential of a protein can be determined by various methods, such as by calculation from the equilibrium constant of the redox reaction involving a reference with known redox potential using the Nernst equation. The commonly used references are defined glutathione/glutathione disulfide (GSH/GSSG) buffers or NADPH/NADP+ coupled via an appropriate reductase (Gilbert H. F. (1990) *Adv. Enzymol. Relat. Areas Mol. Biol.* 63:69). Another method is set forth in Krause et al. (1991) *J. Biol. Chem.* 299: 9494. A preferred method for determining redox potentials of proteins, e.g., members of thioredoxin superfamily and variants thereof, is described in Aslund et al. (1997) *J. Biol. Chem.* 272: 30780 and in Mossner et al. (1998) *Prot. Sci.* 7:1233. Briefly, this method of pair-wise equilibration described in Aslund et al. (1997) for obtaining $E^{o\prime}$ is based on accurate determinations of the equilibrium constant, $K_{12}$ for the reversible thiol-disulfide exchange reaction between various pairs of redox active proteins. Standard state redox potentials are then obtained through equilibration with known standards, e.g., either Trx"PDI" or Trx, whose redox potential has been determined independently (Krause et al. (1991) *J. Biol. Chem.* 266:9494) via coupling to NADPH ($E^{o\prime}=-315$ mV).

In certain cases, the redox potential of a protein is linked to its pKa value. For example, in the case of DsbA, a linear correlation between redox potential and the pKa value of the nucleophilic thiol of the active site has been demonstrated (Krause et al. (1991) *J. Biol. Chem.* 266:9494). Apparently, a major function of the active site motif (CX1X2C) is to modulate the pKa value of the nucleophilic thiol and thereby the stability of the reduced form of the protein relative to the oxidized form. Thus, in the case of DsbA, the very low pKa value of 3.5 (Nelson et al. (1994) *Biochemistry* 33:5974) is an important factor for its highly oxidizing properties. Accordingly, the identification of a protein, e.g., a thioredoxin variant, having oxidizing properties may be identified by the selection of a variant having a low pKa value. The pKa can be determined by methods known in the art, and described, e.g., in Nelson et al., supra.

When expressing variants of wild-type thioredoxin and glutaredoxin enzymes, it may be desirable to inactivate or to inhibit the corresponding endogenous wildtype enzymes in the host cell. This is preferably achieved by introducing null mutations into the corresponding wild type genes. Alternatively, this can be achieved by including into the growth medium of the host cells, a compound which blocks their expression or their activity.

Another catalyst of disulfide bond formation that can be used in the invention is the protein disulfide isomerase (PDI), which is a protein which catalyzes disulfide bond formation in eukaryotes. PDI has been implicated in the catalysis of disulfide bond formation and rearrangement through in vitro data (Creighton et al. (1980) *J. Mol. Biol.* 142:43; Feedman et al. (1989) *Biochem. Soc. Symp.* 5:167; and Bardwell and Beckwith (1993) *Cell* 74:899. Yeast mutants in PDI have been shown to have a defect in the formation of disulfide bonds in carboxypeptidase Y (LaMantia and Lennarz (1993) *Cell* 74:899). Use of PDI for expression of heterologous proteins in host cells is further described in PCT application having publication No. WO 93/25676; WO 94/08012; and EP 509, 841. A variant PDI which can also be used in this invention is disclosed in EP 293,793.

Yet another protein or derivative thereof that can be used as a catalyst in the invention is the glutaredoxin-like protein NrdH, present in, e.g., *E. coli, Lactocuccus Lactis*, and *Salmonella typhimurium*, described in Jordan et al. (1997) *J. Biol. Chem.* 272:18044. This enzyme is reduced by thioredoxin reductase, but not by glutathione.

Homologs, variants, and in particular, enzymes of interest can be obtained from various species or genuses by hybridization techniques or using cross-reacting antibodies. It is known that catalysts of disulfide bond formation and isomarization are relatively well conserved among species, and one could thus, using a sequence from one species, clone the sequence from another species. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a nucleic acid of the present invention will bind to that of another species under moderately stringent conditions, for example at about 2.0×SSC and about 40° C.

Additional catalysts of disulfide bond formation and/or isomerization can be isolated, e.g., by identifying additional substrates of reductases, e.g., thioredoxin reductase and glutathione oxidoreductase. Additional variants of known substrates of reductases and catalysts of disulfide bond formation can be can be identified and prepared by a variety of methods known in the art. These methods include, but are not limited to, in vivo methods, as well as the following in vitro methods: preparation by oligonucleotide-mediated (or site-directed) mutagenesis, alanine-scanning mutagenesis, random mutagenesis, PCR mutagenesis, and cassette mutagenesis of an earlier prepared variant or a wild type protein. Alternatively, such variants can be isolated by screening of a library of variants.

In designing variants, it may be useful to align the sequence of the members of the thioredoxin superfamily, e.g., as shown in Jordan et al., supra, and in FIG. 2 of Aslund et al. (1996) *J. Bio. Chem.* 271: 6736. The knowledge of the redox potential, and other characteristics of these enzymes will then allow the determination of which amino acid should be conserved and of those amino acids which can be modified to maintain, or alternatively modify certain characteristics of a member of the family. In particular, as further described herein, modification of the C-Xaa-Xaa-C (SEQ ID NO: 1) active site of a member is likely to affect its redox potential. The effect of the modifications on the redox potential can be determined as further described herein, and in Aslund et al. (1997) supra. Variants having a specific characteristic, e.g., a specific redox potential, can be screened for.

In a preferred embodiment, a thioredoxin variants having an enhanced activity are identified by in vivo techniques, e.g., in vivo genetic screens for selection of mutants that are enhanced. Such methods can comprise looking for those variants which when expressed or overexpressed in a host cell enhance the production of properly folded test protein, e.g., tPA.

Set forth below are in vitro methods for modifying thioredoxin family members or catalysts. Oligonucleotide-mediated mutagenesis represents a preferred method for preparing substitution, deletion, and insertion variants of genes, although other methods may be utilized as desired. This technique is well known in the art as described by Zoller and Smith, *Nucleic Acids Res.*, 10: 6487 (1982). Briefly, DNA is altered by hybridizing an oligonucleotide encoding the desired mutation to a DNA template, where the template is the single-stranded form of a plasmid or bacteriophage containing the unaltered or native DNA sequence. After hybridization, a DNA polymerase is used to synthesize an entire second complementary strand of the template that will thus incorporate the oligonucleotide primer, and will code for the selected alteration in the DNA.

Generally, oligonucleotides of at least 25 nucleotides in length are used. A preferred oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci USA*, 75: 5765 (1978). The DNA template can be generated by those vectors that are either derived from bacteriophage M13 vectors (the commercially available M13 mp18 and M13 mp19 vectors are suitable), or those vectors that contain a single-stranded phage origin of replication as described by Viera et al., *Meth. Enzymol.*, 153: 3 (1987). Thus, the DNA that is to be mutated may be inserted into one of these vectors to generate single-stranded template. Production of the single-stranded template is described in Sections 4.21-4.41 of Sambrook et al., Molecular Cloning: A Laboratory Manual (Cold Spring Harbor Laboratory Press, NY 1989). Alternatively, a single-stranded DNA template may be generated by denaturing double-stranded plasmid (or other) DNA using standard techniques.

A useful method for identification of certain residues or regions of a protein, such a thioredoxin, glutaredoxin, isomerase or other catalyst of disulfide bond formation that are preferred locations for mutagenesis is called "alanine-scanning mutagenesis," as described by Cunningham and Wells, *Science*, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the expressed variants are screened for the most preferred combination of desired activity.

For alteration of the native DNA sequence (to generate amino acid sequence variants, for example), the preferred method is the combination of oligonucleotide-directed mutagenesis and random mutagenesis as described by Kunkel et al., *Methods Enzymol.*, 154: 367 (1987). In this method, oligonucleotide-directed mutagenesis is employed to randomize particular codons of the wild-type gene to encode all possible residues. A pool of oligonucleotides with complementary sequence (about 10-15 bases) flanking the codon of choice is used. The codon of choice is replaced with the nucleotides NNS, where N is any nucleotide and S is G or C, to give a pool of oligonucleotides encoding all possible amino acids in 32 codons.

In this preferred method, a pBR322-derived plasmid with a single-stranded origin of replication is prepared as a single-stranded plasmid template in an *E. coli* dut-ung-strain such as CJ236 (Kunkel et al., supra). These two mutations in the strain cause the incorporation of one or more uracil nucleotides into the single-stranded DNA instead of thymine. The random oligonucleotides are annealed, filled in with *E. coli* phage T7 DNA polymerase, ligated, and transformed into a wild-type strain of *E. coli* such as W3110 or strain 13G8 (W3110 tonA DELTA PhoS64). The latter strain is negative for the particular gene and derived from CGSC6777 (C75-b), which is derived from C75, described by Amemura et al., *J. Bacter.*, 152: 692-701 (1982). The wild-type strain corrects the uracil misincorporation using the synthetic mutant strand as a template so as to produce about 90% mutants.

DNA encoding mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of a thioredoxin, glutaredoxin, DsbC or other catalyst of disulfide bond formation and/or isomerization. While the following discussion refers to DNA, it is understood that the technique also finds application with RNA. The PCR technique generally refers to the following procedure (see Erlich, supra, the chapter by R. Higuchi, p. 61-70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

Another method for preparing variants, cassette mutagenesis, is based on the technique described by Wells et al., *Gene*, 34: 315 (1985). The starting material is the plasmid (or other vector) comprising the DNA to be mutated. The codon(s) in the DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence.

Nucleic acid encoding the variant may also be chemically synthesized and assembled by any of a number of techniques, prior to expression in a host cell. (See, e.g., Caruthers, U.S. Pat. No. 4,500,707; Balland et al., *Biochimie*, 67: 725-736 (1985); Edge et al., *Nature*, 292: 756-762 (1982)).

A DNA variant typically may be made by random and/or site-specific mutagenesis of the native-encoding nucleic acid and transfection or integration of the variant gene into the chromosomes of a bacterial host, or by random mutagenesis of a host containing the native gene. The nucleic acid variant may then be screened in a suitable screening assay for the desired characteristic.

Catalysts of disulfide bond isomerization must be in a reduced state to be active and must be able to reduce a substrate. Several methods can be used to determine whether an enzyme is capable of reducing a substrate, or more specifically reduce the disulfide bond(s) of a substrate. These are set forth below.

The reducing capacity of an enzyme, e.g., a thioredoxin variant, can be measured using the beta-hydroxyethylene disulfide (HED) reduction assay (Holmgren et al. (1979) *J. Biol. Chem.* 254, 3664).

Another method for determining the reducing capacity of an enzyme is by the in vitro reduction of insulin disulfides, which can be monitored spectrophotometrically as described previously (Luthman and Holmgren (1982) *J. Biol. Chem.* 257:6686 and Moessner et al. (1999) *J. Biol. Chem.* 274: 25254). Briefly, bovine pancreas insulin (Sigma, final concentration 0.1 mM) is added to cuvettes containing 0.5 ml of 1 mM GSH, 0.2 mM NADPH, 10 µg/ml glutathione reductase, 0.1 mg/ml bovine serum albumin, and 50 mM Tris-Cl at pH 8.0. The reaction is started by the addition of the different enzymes to be assayed and monitored by measuring the consumption of NADPH at 340 nm for 10 min at 25° C.

Alternatively, the reducing capacity of an enzyme is determined in a Ribonucleotide Reductase Activity, as described, e.g., in Thelander et al., (1978) *Methods Enzymol.* 51: 227, and Holmgren (1979) *J. Biol. Chem.* 254: 9113, by monitoring the conversion of [$^3$H]CDP to [$^3$H]dCDP by 10 µg of ribonucleotide reductase. Reducing equivalents can be provided through 4.0 mM GSH, 1.0 mM NADPH, and 0.01 mg/ml glutathione reductase. Incubations are performed in the presence of either 1.0 µM Grx1 or 0.35 µM Grx3.

Other substrates that can be used for determining the reducing capacity of an enzyme include lipoic acid and oxidized DTT. Such assays are described, e.g., in Moessner et al. (1999) *J. Biol. Chem.* 274: 25254.

Several methods can be used to assess disulfide bond isomerization in vitro. In an illustrative embodiment, the disulfide bond isomerization capability of an enzyme is measured by the ability of the enzyme to isomerize a misoxidized form of bovine pancreatic trypsin inhibitor (BPTI) (Zapun et al. (1995) *Biochemistry* 34: 5075).

Assays for determining the ability of an enzyme to catalyze the formation of disulfide bonds are set forth, e.g., in Zapun and Creighton (1994) *Biochemistry* 33: 5202 and Jonda et al. (1999) *EMBO J.* 18: 3271. Typically, an enzyme and a reduced substrate are incubated together and the amount of reduced and oxidized substrates is determined, e.g., HPLC or Mass Spectrometry. A substrate protein is, e.g., a ribonuclease or hirudin.

Characteristics of enzymes, e.g., the $K_M$ (Michaelis Menten constant), Vmax, Kcat, and kcat/$K_M$, can be determined according to methods known in the art, e.g., as described in Moessner et al. (1999) *J. Biol. Chem.* 274: 25254. Preferred enzymes have a $K_M$ with a substrate of with a reductase which reduces them, of at least about $10^{-1}$ $M^{-1}$, preferably at least about $10^{-2}$ $M^{-1}$, at least about $10^{-3}$ $M^{-1}$, at least about $10^{-4}$ $M^{-1}$, at least about $10^{-5}$ $M^{-1}$, at least about $10^{-6}$ $M^{-1}$, and most preferably at least about $10^{-7}$ $M^{-1}$. Preferred enzymes, e.g., thioredoxin variants, have a rate constant (kcat) in a reaction with a substrate or a reductase that reduces them, of about 40 $s^{-1}$ or less, preferably 35 $s^{-1}$ or less, preferably 30 $s^{-1}$ or less, preferably 25 $s^{-1}$ or less, preferably 20 $s^{-1}$ or less, preferably 15 $s^{-1}$ or less, preferably 10 $s^{-1}$ or less, or even more preferably 5 $s^{-1}$ or less. Preferred enzymes have a kat/$K_M$ of about $10^7$ $M^{-1}$ $s^{-1}$, or about $1,5 \times 10^7$, about $2 \times 10^7$, or about $2.5 \times 10^7$.

Secondary structure analysis using NMR can be performed as described in Aslund et al. (1996) *J. Biol. Chem.* 271: 6736.

Several of the assays described in this section require the use of isolated protein, e.g., a thioredoxin variant or a reductase, such as obtained by in vitro production. Preparation and purification of these enzymes are described in numerous articles, including articles cited herein.

Additional Modifications to the Host Cells

Host cells of the invention can further be modified to improve the synthesis or folding of the polypeptides of interest.

In one embodiment, a host cell is further modified to express a chaperone protein, which assists in the folding of the protein of interest. A chaperone can be, for example, a heat-shock protein, such as the heat-shock sigma factor, e.g., the heat-shock factor sigma$_{32}$ encoded by the gene rpoH (Wulfing and Pluckthun (1994) *Mol. Microbiol.* 12:685). For example, Wulfing and Pluckthun have produced functional fragments of the T cell receptor (TCR) in the periplasm of *E. coli* by overproduction of this heat-shock factor. WO 94/08012 also describes the describes the production of a heterologous protein by coexpressing of a chaperone, such as a heat-shock factor. Another heat shock factor which can be coexpressed for its chaperone properties, is Hsp33, a member of the heat shock family of proteins (Jakob et al. (1999) *Cell* 96:341).

Methods and Materials for Modifying Host Cells

A person of skill in the art will readily know how to modify host cells, such as prokaryotic cells, e.g., *E. coli* cells, to obtain the host cells described herein, according to methods in prokaryotic genetics. Similarly, methods for expressing polypeptides in host cells are well known in the art. Furthermore some partially modified host cells can be commercially purchased. For example, Novagen makes available various bacterial strains containing a null mutation in the trxA and/or the trxB genes. For example, Novagen strain AD494 lacks the thioredoxin reductase (trxB) gene.

The nucleotide and amino acid sequences of the genes to be mutated, or overexpressed in a host cell are publicly available, e.g., in GenBank, and are described in numerous references. Nucleic acids to be mutated or overexpressed and host cells, such as bacterial strains, can be obtained at the ATCC, or can be purchased from commercial vendors, e.g, Novagen.

However, for simplicity, methods of producing modified prokaryotic cells are briefly set forth below.

A nucleic acid (e.g., cDNA or genomic DNA) encoding a protein of interest, a catalyst, or chaperone, or other protein can be suitably inserted into a replicable vector for expression in the prokaryotic cell under the control of a suitable prokaryotic promoter. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes, and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene*, 2: 95 (1977)). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

The DNA encoding the polypeptide of interest herein may be expressed not only directly, but also as a fusion with another polypeptide, such as a polypeptide from the host cell.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide or catalyst of disulfide bond formation and/or isomerization may also contain an inducible promoter that is recognized by the host bacterial organism and is operably linked to the nucleic acid encoding the polypeptide of interest or the catalyst. Inducible promoters suitable for use with bacterial hosts include the beta-lactamase and lactose promoter systems (Chang et al., *Nature*, 275: 615 (1978); Goeddel et al., *Nature*, 281: 544 (1979)), the arabinose promoter system (Guzman et al., *J. Bacteriol.*, 174: 7716-7728 (1992)), alkaline phosphatase, a tryptophan (trp) promoter system (Goeddel, *Nucleic Acids Res.*, 8: 4057 (1980) and EP 36,776) and hybrid promoters such as the tac promoter (deBoer et al., *Proc. Natl. Acad. Sci. USA*, 80: 21-25 (1983)). However, other known bacterial inducible promoters are suitable. Their nucleotide sequences have been published, thereby enabling a skilled worker operably to ligate them to DNA encoding the polypeptide of interest or the catalyst encoding genes (Siebenlist et al., *Cell*, 20: 269 (1980)) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures can be used to transform *E. coli* K12 strain 294 (ATCC 31,446) or other strains, and successful transformants can be selected by ampicillin or tetracycline resistance where appropriate. Plasmids from the transformants can be prepared, analyzed by restriction endonuclease digestion, and/or sequenced by the method of Sanger et al., *Proc. Natl. Acad. Sci. USA*, 74: 5463-5467 (1977) or Messing et al., *Nucleic Acids Res.*, 9: 309 (1981) or by the method of Maxam et al., *Methods in Enzymology*, 65: 499 (1980).

Host cells are transfected, and preferably transformed with the above-described expression vectors of this invention and cultured in conventional nutrient media modified as appropriate for inducing the various promoters.

Transfection refers to the taking up of an expression vector by a host cell whether or not any coding sequences are in fact expressed. Numerous methods of transfection are known to the ordinarily skilled artisan, for example, $CaCl_2$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., Molecular Cloning: A Laboratory Manual [New York: Cold Spring Harbor Laboratory Press, 1989], is generally used for bacterial cells that contain substantial cell-wall barriers. Another method for transformation employs polyethylene glycol/DMSO, as described in Chung and Miller, *Nucleic Acids Res.*, 16: 3580 (1988). Yet another method is the use of the technique termed electroporation.

In an exemplary embodiment, insertion of a gene of interest or a gene encoding a catalyst of disulfide bond formation and/or isomerization into the host genome includes using a vector for transformation which contains a DNA sequence that is complementary to a sequence found in the genonmic DNA of the host cell. Transfection of the host cell, e.g., *E. coli*, with this vector results in homologous recombination with the genome and insertion of the gene. As a result of the transformation, the host cell is either negative for that particular gene (is a null mutant of that particular gene) or has its wild-type gene replaced by a variant gene upon integration thereof. Accordingly, the same technique can also be used to mutate a particular gene in a host cell, i.e., to obtain a null mutant of that gene.

Assays for Determining the Efficiency of the Host Cells in Producing Properly Folded Proteins Having at Least One Disulfide Bond Various methods for determining the extent of proper disulfide bond formation in the cytoplasm of a bacteria can be used. In one method, the bacteria are transformed with a gene encoding a polypeptide (a "test" polypeptide) which normally contains at least one disulfide bond. Preferred test polypeptides or proteins are those which are normally secreted from cells or which are membrane proteins. For use in the assays described herein, these polypeptides are modified by the deletion or mutation of the signal sequence, such that the proteins are not exported outside of the cytoplasm of the cell.

Preferably the test comprises expressing a complicated polypeptide, i.e., having multiple disulfide bonds, e.g., tPA or urokinase (see Examples). Preferably, the test polypeptide lacks a biological activity when it does not have properly formed disulfide bonds. For example, alkaline phosphatase and urokinase proteins require disulfide bonds to be active. Thus, when these proteins are expressed in the cytoplasm of wild type bacteria, no disulfide bonds are formed, and these proteins are not active. Biological activity tests for these proteins are commercially available (see Examples).

If desired, various methods can be used to determine whether a gene of interest is expressed in a host cell. For example, expression of the protein can be determined by conventional Northern blotting to quantitate the transcription of mRNA. Various labels may be employed, most commonly radioisotopes. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

Moreover, when antibodies reactive against a given gene product are available, such antibodies can be used to detect the gene product in any known immunological assay (e.g., as in Harlowe et al., Antibodies: A Laboratory Manual, Cold Spring Harbor Laboratory Press, New York, 1988). The gene product can also be detected using tests that distinguish polypeptides on the basis of characteristic physical properties such as molecular weight. To detect the physical properties of the gene product, all polypeptides newly synthesized by the host cell can be labeled, e.g., with a radioisotope. Common radioisotopes that can be used to label polypeptides synthesized within a host cell include tritium ($^3H$), carbon-14 ($^{14}C$), sulfur-35 ($^{35}S$), and the like. For example, the host cell can be grown in $^{35}S$-methionine or $^{35}S$-cysteine medium, and a significant amount of the $^{35}S$ label will be preferentially incorporated into any newly synthesized polypeptide, including the over-expressed heterologous polypeptide. The $^{35}S$-containing culture medium is then removed and the cells are washed and placed in fresh non-radioactive culture medium. After the cells are maintained in the fresh medium for a time and under conditions sufficient to allow secretion of the $^{35}S$-radiolabeled expressed heterologous polypeptide, the culture medium is collected and separated from the host cells. The molecular weight of the secreted, labeled polypeptide in the culture medium can then be determined by known procedures, e.g., polyacrylamide gel electrophoresis. Such procedures, and/or other procedures for detecting secreted gene products, are further described in the Examples, and are also provided in Goeddel, D. V. (ed.) 1990, *Gene Expression Technology, Methods in Enzymology*, Vol. 185 (Academic Press), and Sambrook et al., supra.

A factor which may predict the ability of a modified host cell to produce disulfide bond containing proteins is the redox potential of the cytoplasm of the host cell. There are currently many different methods to measure cellular redox status, e.g., as described in Gilbert et al. (1990) *Adv. Enzymol. Rel. Areas Mol. Biol.* 63:69; Holmgren and Fgestedt (1982) *J. Biol. Chem.* 257: 6926; and Hwang et al. (1992) *Science* 257: 1496.

Exemplary Methods of Practicing the Invention

In an illustrative embodiment, disulfide bond containing proteins of the invention are produced as follows. A host cell or organism of the invention is first transformed with an expression plasmid encoding a polypeptide of interest and a selection marker. The plasmid can encode additional polypeptides, such as is desired, e.g., in the production of multi-polypepeptide proteins. Additional plasmids encoding other polypeptides can be co-transformed, or transformed separately into the host cell or ogranism. When using more than one plasmid, it may be preferable to use different markers of selection, to insure that all the desired plasmids are contained in the recombinant host cell that is selected. Following transformation of the one or more plasmids into the host cells, according to known methods, clones having taken up the plasmid(s) are selected on appropriate medium, and cloned. Separate clones are then tested to confirm that they have the desired characteristics, including the expression of the one or more polypeptides. In particular, the polypeptide(s) of interest can be isolated from the host cells, and tested for activity, amount, etc. The isolated clones can then be frozen in aliquots for preservation, pursuant to methods well known in the art.

Once a clone of the host cell expressing the protein of interest has been obtained, the cloned host cell can be grown in large cultures to produce large amounts of the protein of interest, from which the polylpeptide(s) of interest can be isolated.

The polypeptide of interest can, e.g., be produced by growing the host cells expressing the protein of interest in shaker flasks, as described, e.g., in Qui et al. (1998) *Appl. Environ. Microbiol.* 64:4891. Briefly, the host cells containing a plasmid encoding the protein of interest are grown in Luria-Bertani medium at 37° C. supplemented with selection drugs, e.g., amplicillin (100 µg/ml), kanamycin (40 µg/ml), and chloramphenicol (20 µg/ml). The synthesis of a protein whose expression is under the control of an inducible promoter (e.g., the protein of interest or a catalyst of disulfide bond formation) can then be induced by the addition of an inducer, e.g., IPTG (2 mM final) when the culture optical density at 600 nm ($OD_{600}$) reached between 0.8 and 1.0. After induction, cultures are grown for approximately three more hours, and the harvested by centrifugation. The cells can then be resuspended in 0.1 M Tris-HCl (pH 8.5) and lysed with a French pressure cell operated at 2,000 lb/in². Subsequently the cell lysates can be centrifuged at 12,000×g for about 10 minutes at 4° C. to separate the soluble and insoluble fractions.

The polypeptide of interest can also be produced in fermentators, as described, e.g., in Qui et al. (1998) *Appl. Environ. Microbiol.* 64:4891. Briefly, 1 ml of frozen host cells containing a plasmid encoding the protein of interest are used to inoculate 500 ml of Luria-Bertani medium containing the appropriate antibiotic. The culture is grown in a 2 liter flask for 10 hours, reaching an $OD_{550}$ of about 3.0. This inoculum culture is then added to approximately 6.5 liters of mineral salts medium containing 1.2% digested casein, 1.2% yeast extract, and 1.5 g of isoleucine and 1 g of glucose per liter in a 15 liter Biolafite fermentor. The fermentor is operated at 37° C. and 1,000 rpm, with 10 standard liters per minute of aeration and a 0.3 bar back pressure to deliver an oxygen transfer rate of approximately 3.0 mmol/liter-min. When the initial glucose was depleted, a concentrated glucose solution can be added to maintain a growth rate of $0.32$ $h^{-1}$ until the dissolved oxygen concentration ($DO_2$) reached 30% of air saturation. At that point glucose feeding is adjusted to maintain a $DO_2$ of 30%. At an $OD_{550}$ of 25, a feed consisting of 13.5% digested casein and 6.5% yeast extract is added at 0.5 m./min. When the $OD_{550}$ reaches 80, IPTG or other inducer (if needed) is added at a concentration of 0.05 mM, and other inducers, e.g., arabinose (0.1% final) can be added, as needed. When respiration poisoning causes the $DO_2$ to rise, the glucose feed rate can be lowered to avoid excessive acetate accumulation.

A method for isolating the protein of interest, e.g., tPA, from the culture of host cells is described in Qui et al. (1998), supra. Methods for quantitating tPA activity is also described in Qui et al. (1998), supra.

The host cells of the invention are preferably capable of producing a properly folded protein of interest to a level that is at least two fold higher, at least 3 fold, at least 5 fold, at least 10 fold, at least 20 fold, at least 50 fold, 100 fold higher, at least $10^4$, $10^5$, $10^6$ or more fold higher relative to the production of properly folded protein in the periplasm of the same cell or relative to its production in the wildtype cell or in a partially modified cell (i.e., a cell that has only some of the modifications, e.g., null mutations, or inserted genes).

Other methods, assays, and materials that may be useful in practicing the invention are provided in the literature, in particular, in the following references: Debarbieux and Beckwith (1998) *PNAS* 95: 10751; Qui et al. (1998) *Applied Environm. Microbiol.* 64: 4891; Derman et al. (1993) *Science* 262: 1744; Prinz et al. (1997) *J. Biol. Chem.* 272: 15661; Stewart et al. (1998) *EMBO J.* 17: 5543; Aslund et al. (1999) *PNAS* 274: 25254; and Moessner et al. (1999) *J. Biol. Chem.* 274: 25254.

Polypeptides and Compositions of the Invention

The invention provides polypeptides expressed in heterologous host cells modified as described herein to produce high levels of properly folded polypeptides or proteins having at least one disulfide bond. In addition, since certain proteins, which do not have disulfide bonds when they are completely synthesized, pass through an intermediate structure having at least one disulfide bonds (see Background of the Invention), the instant invention is also useful for producing such proteins. The polypeptides can also have at least 2, at least 3, 4, 5, 6, 7, 8, 9, 10, 12, or 15 disulfide bonds, or more. However, as shown herein, the invention can also be used in producing proteins having at least 17 disulfide bridges, at least 20, at least 25, or at least 30 disulfide bridges. The system of the invention can efficiently produce properly formed and active proteins having any number of disulfide bonds. The system of the invention can also be used for the production of proteins having multiple polypeptide chains that are linked through one or more disulfide bonds.

The polypeptides of the invention are preferably at least about 30% pure, at least about 40%, 50%, 60%, 70%, 80%, 90%, or even more preferably at least about 95% pure. Yet, even more preferred polypeptides of the invention are at least 97%, 98%, or 99% pure. The purity of a preparation is defined relative to the amount of material from the same organism. Thus, for example, a preparation of a particular polypeptide that is 98% pure contains at most 2% of material from the organism in which the polypeptide was produced.

In an even more preferred embodiment, the protein or polypeptide of the invention contains less than 0.1%, preferably less than $10^{-2}$%, less than $10^{-3}$%, less than $10^{-4}$%, less than $10^{-5}$% or even more preferably less than $10^{-6}$% of eukaryotic cellular material. In fact, since the invention allows the production of high quantities of biologically active proteins in bacteria, these proteins can be produced free of eukaryotic material.

Thus, the invention provides compositions, e.g., pharmaceutical compositions, comprising proteins produced according to the method of the invention. These compositions differ from previous preparations of the same type of protein in that, until now it has not been possible to produce correctly folded complicated disulfide bond containing proteins in high yields in prokaryotes, and thus, it has not previously been possible to obtain these proteins completely devoid of any eukaryotic cellular material. Thus, the proteins produced in prokaryotes according to the methods of the invention are particularly useful for administration into humans, in view of the strict FDA requirements.

The polypeptides are preferably produced at an efficiency of at least about 1, 5, 10, 15, 20, 25, 30, 40, or more preferably at least about 50 mg/l of host cell culture.

Preferred polypeptides or proteins which can be produced according to the methods of the invention include any protein containing at least one disulfide bond, or which, in the mature form does not contain a disulfide bond, but a precursor of which contained at least one disulfide bond. Since most disulfide bond containing proteins are secreted or membrane proteins, preferred proteins of the invention are secreted or membrane proteins. The proteins can be eukaryotic, prokaryotic proteins, viral proteins, or plant proteins. Preferred proteins are of mammalian origin, and even more preferably of human origin. However, they can also be of murine, bovine, ovine, feline, porcine, canine, goat, equine, and primate origin.

Additional examples of proteins of interest which can be produced include the following proteins: mammalian polypeptides including molecules such as, e.g., renin, growth hormone, including human growth hormone; bovine growth hormone; growth hormone releasing factor; parathyroid hormone; thyroid stimulating hormone; lipoproteins; alpha 1-antitrypsin; insulin A-chain; insulin B-chain; proinsulin; thrombopoietin; follicle stimulating hormone; calcitonin;

luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; kallikreins; protease inhibitors; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; gonadotropin-associated peptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-beta; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The system is also particularly useful in the production of antibodies, such as single chain antibodies, as well as antibodies consisting of multiple polypeptide chains.

The polypeptides and proteins of the invention can be used for a great variety of purposes. Preferred uses include medical uses, including diagnostic uses, prophylactic and therapeutic uses. For example, the proteins can be prepared for topical or other type of administration. Another preferred medical use is for the preparation of vaccines. Accordingly, the proteins of the invention are solubilized or suspended in pharmacologically acceptable solutions to form pharmaceutical compositions for administration to a subject. Appropriate buffers for medical purposes and methods of administration of the pharmaceutical compositions are further set forth below. It will be understood by a person of skill in the art that medical compositions can also be administered to subjects other than humans, such as for veterinary purposes.

Examples of diagnostic uses include the use of a protein of the invention as a binding agent, to detect specific proteins or DNA in a cell sample or on a tissue section. Preferred proteins of the invention for this purpose include antibodies. Diagnostic methods using antibodies or other binding agents are well known in the art and include flow cytometry, ELISA, and immunohistochemical methods.

Proteins of the invention can also be used for research purposes, e.g., in research laboratories. In particular, at least some proteins of the invention can be used as molecular weight markers.

Yet other proteins produced according to the method of the invention can be used as nutritional sources or supplements. Such uses include without limitation use as a protein or amino acid supplement, use as a carbon source, use as a nitrogen source and use as a source of carbohydrate. In such cases the protein of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

A protein of the invention be used in one or more of the following purposes or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or bodypart size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in vaccine composition to raise an immune response against such protein or another material or entity which is cross-reactive with such protein.

Effective Dose and Administration of Therapeutic Compositions

Toxicity and therapeutic efficacy of compounds of the invention can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Kits of the Invention

For any of the above-described uses, including any or all of these research utilities, the proteins can be commercialized as part of a kit, e.g., a kit of research products. Such a kit can comprise one or more proteins produced according to the method of the invention, and any additional reagent, e.g., a buffer, a control reagent, and an antibody against the protein.

In another embodiment, the kit comprises a host cell of the invention and optionally an inducer, growth media, a plasmid encoding a protein of interest, a probe, an antibody, and/or instructions for use. Thus, a kit may contain one or more necessary components for producing a biologically active or properly folded disulfide containing protein. Accordingly, a kit may comprise a host cell and instructions for use. Alternatively, a kit may comprise one or more reagents necessary for the preparation of a host cell of the invention. Such a kit may comprise agent(s) for reducing the expression of reductases or agents necessary for introducing mutations into one or more reductases of a host cell. A kit may comprise agents necessary for improving the growth of host cells, e.g., reducing agents, or a gene optionally contained in a plasmid, encoding a protein which improves growth, e.g., AhpC*.

The present invention is further illustrated by the following examples which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Isolation of trxB gshA supp and trxB gor Suppressor Strains

This Example describes the isolation of suppressor mutants of the trxB gshA and trxB gor mutants, which grow at about the same rate as their wild type parental strain *E. coli* DHB4.

For aerobic growth, *E. coli* depends on the presence of either of the two major thiol reduction systems—the thioredoxin and the glutathione-glutaredoxin pathways. When both of these pathways are eliminated by mutation, such as in a trxB gor or trxB gshA double mutant, the cells grow extremely slowly (Prinz, et al. (1997) *J. Biol. Chem.* 272: 15661). These cells can, however, be rescued by the addition of the reductant DTT to the growth medium.

When grown in the presence of DTT, both the trxB gshA and trxB gor strains give rise to fast growing derivatives at a high frequency. Since the trxB, gshA, and gor alleles in these strains are non-reverting null mutations, the faster growing derivatives must result from extragenic suppressor mutations.

Two fast growing suppressor mutants were obtained from the strains DHB4 gshA20::Tn10 Km trxB::Km . . . Tn10 and DHB4 gor522 . . . mini-Tn10Tc trxB::Km, both of which are derivatives of DHB4 (MC1000 phoA(PvuII) phoR malF3 F'[lac+(lacIQ) pro]) (Boyd, et al. (1987) *Proc Natl Acad Sci USA* 84: 8525), as follows. These fast growing suppressor mutants were obtained by growing the two strains for about 24 hours in medium containing 6 mM DTT. A fast growing strain from each of the two strains were isolated: FA112 ((DHB4 gshA20::Tn10 Km trxB::Km . . . Tn10 supp) and FA113 (DHB4 gor522 . . . mini-Tn10Tc trxB::Km supp). Each of these strains was deposited at the ATCC on Nov. 11, 1999 under the requirements and terms of the Budapest Treaty, and have been assigned Accession Nos. PTA-938 (FA112) and PTA-939 (FA113), respectively.

Figure 3:
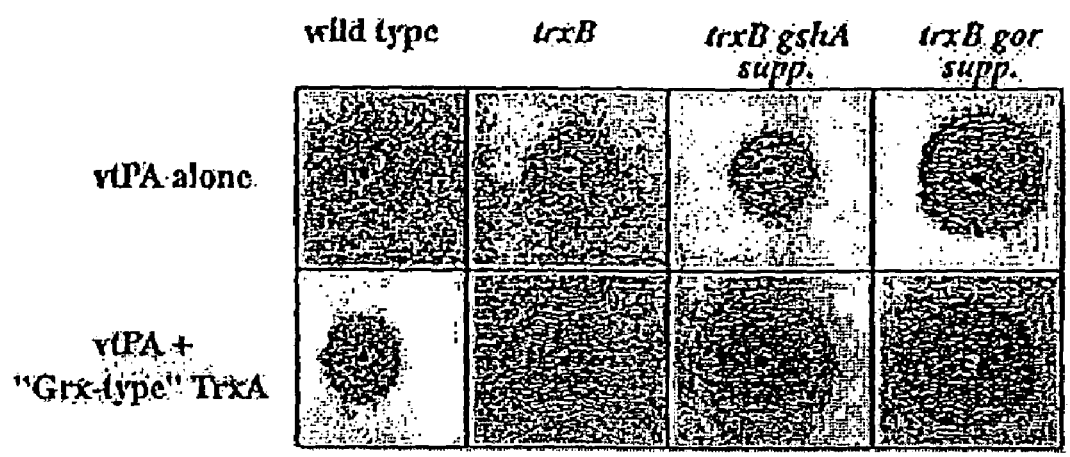
FIG. 3 shows the clearing zones obtained from a fibrinolysis assay showing tPA activity in DHB4 (wild type), WP597 (trxB), FA112 (trxB gshA supp), and FA113 (trxB gor supp) cells transformed with a plasmid encoding tPA devoid of signal sequence (plasmid pTrcvtPA; top row) or in the same cells further cotransformed with a "Grx-type" variant TrxA (plasmid pFA5; bottom row).

For establishing the growth curve of the FA113 strain and compare it to its wild type parent strain, the bacteria were subjected to aerobic growth at 37° C. in LB medium in test tubes. The results, which are presented in FIG. 3, show that at 37° C. in rich media, FA113 was found to grow almost as well as the wild type (DHB4, trxB+ gor+) strain with doubling times 30 and 27 minutes, respectively. In contrast, WP778, the trxB gor parent of FA113 grew with a doubling time of 300 min in the absence of DTT (Prinz, et al. (1997) *J. Biol. Chem.* 272: 15661).

Example 2

Proper Disulfide Bond Formation of MalS in the Suppressor Strains

This Example demonstrates the production of high amounts of the disulfide bond containing protein MalS in the cytoplasm of a suppressor mutant.

For determining whether any of the suppressed mutants still retains the high cytoplasmic oxidizing potential of the parental trxB gshA (FA112) or trxB gor (FA113) strains, the production of a variety of model proteins was tested. Accordingly, a signal sequenceless version of MalS, a periplasmic amylase that contains 2 disulfide bonds, was expressed in FA112 and FA113. This construct is described Spiess et al. (1999) *Cell* 97: 339. The amount and activity of the MalS enzyme produced by the two strains was determined as described in Spiess et al. (1999) *Cell* 97: 339. The results indicate that enzymatically active protein was detected only in the trxB gor supp strain FA113.

Example 3

Proper Disulfide Bond Formation of Multiple Disulfide Bond Containing Proteins in the Suppressor Strains This Example demonstrates that the following proteins which contain multiple disulfide bonds are produced at high levels and in a proper conformation in the cytoplasm of a suppressor mutant: a version of mouse urokinase with six disulfide bonds only one of which is linear; a truncated form of the human tissue plasminogen activator (vtPA) consisting of the kringle 2 and protease domains with a total of nine disulfide bonds (one linear); and the full-length human tPA containing 17 disulfide bonds and one free cysteine.

The cytoplasmic expression of mouse urokinase devoid of signal sequence, full length human tPA, and human tPA devoid of signal sequence (amino acids 6-175), all of which contain multiple disulfide bonds with non-linear connectivities, was analyzed, and compared to the periplasmic expression of these proteins. The amino acid sequence of human tPA is described in Obukowicz, et al. (1990) *Biochemistry* 29: 9737. For production of full length human tPA, the gene encoding full length human tPA was cloned into plasmid pTrc99A (trc promoter, $Amp^R$, ColE1 ori; Amersham Pharmacia Biotech, Uppsala, Sweden) under the control of the trc promoter, to yield plasmid pTrctPA. A vtPA gene encoding amino acids 6-175 of human tPA was cloned into plasmid pTrc99A under the control of the trc promoter, to yield plasmid pTrcvtPA.

The amount of active urokinase was determined by zymography, as described in Prinz et al. (1997) *J. Biol. Chem.* 272: 15661.

The amount of active vtPA and tPA was determined by fibrin clearance assays as follows. Cells expressing either vtPA or full length tPA were grown with shaking at 30° C. in LB medium supplemented with antibiotics (50 µg/ml Carbenicillin, 25 µg/ml Chloramphenicol) as needed. At OD600 0.8, arabinose was added to 0.2% w/v final concentration; 30 minutes later IPTG was added to 1 mM, and the culture was grown an additional 3 hours. Cells were harvested by centrifugation, resuspended in cold PBS, and lysed in a French pressure cell. The insoluble fractions were removed by centrifugation (12,000×g, 10 min, 4° C.), and soluble protein was quantified by the Bio-Rad (Hercules, Calif.) protein assay, using BSA as standard. Plasminogen activation was quantified by an indirect chromogenic assay as follows. In a microtiter plate, 5 µg of soluble protein was added to wells containing 50 mM Tris-HCl pH 7.4, 0.01% Tween 80, 0.04 mg/ml human glu-plasminogen (American Diagnostica, Greenwich, Conn.), and 0.4 mM Spectrozyme PL® (American Diagnostica); 260 µL final volume. The plate was then incubated at 37° C., and absorbance at 405 nm was read after 2 or 3 hours. Activity is directly proportional to A405 (i.e., absorbance at 405 nm), which is the absorbance after subtracting the background of a strain lacking a vector expressing tPA. Relative activities were normalized to the A405 obtained by expressing vtPA alone in FA113.

In some experiments vtPA and tPA activities were determined by monitoring fibrin clearance as previously described (Qiu, et al. (1998) *Appl. Environ. Microbiol.* 64: 4891; Waldenstrom, et al. (1991) *Gene* 99: 243). Briefly, soluble protein (10 µg) from induced cultures was spotted onto fibrin/agarose plates and incubated for 24 hrs at 37° C. Clearance zones qualitatively measure biological activity of bacterially produced vtPA.

The results, which are shown in FIG. 3, indicated that for all three proteins, substantially higher levels of active protein was detected in FA113 (trxB gor supp.), compared to the wild type, the trxB mutant, or the trxB gshA supp strain FA112. A comparison of the fibrin clearance zones shown in FIG. 3 with a quantitative determination of the protease activity of vtPA using a coupled assay that measures the activation of plasminogen to plasmin revealed that the level of active vtPA in FA113 is 10-fold higher than when expressed in the wild type strain DHB4, and 2.5-fold higher than in the trxB gshA supp strain. Since the trxB gor supp strain, FA113, gave the highest yields of active protein, it was selected for more detailed characterization.

Figure 4:
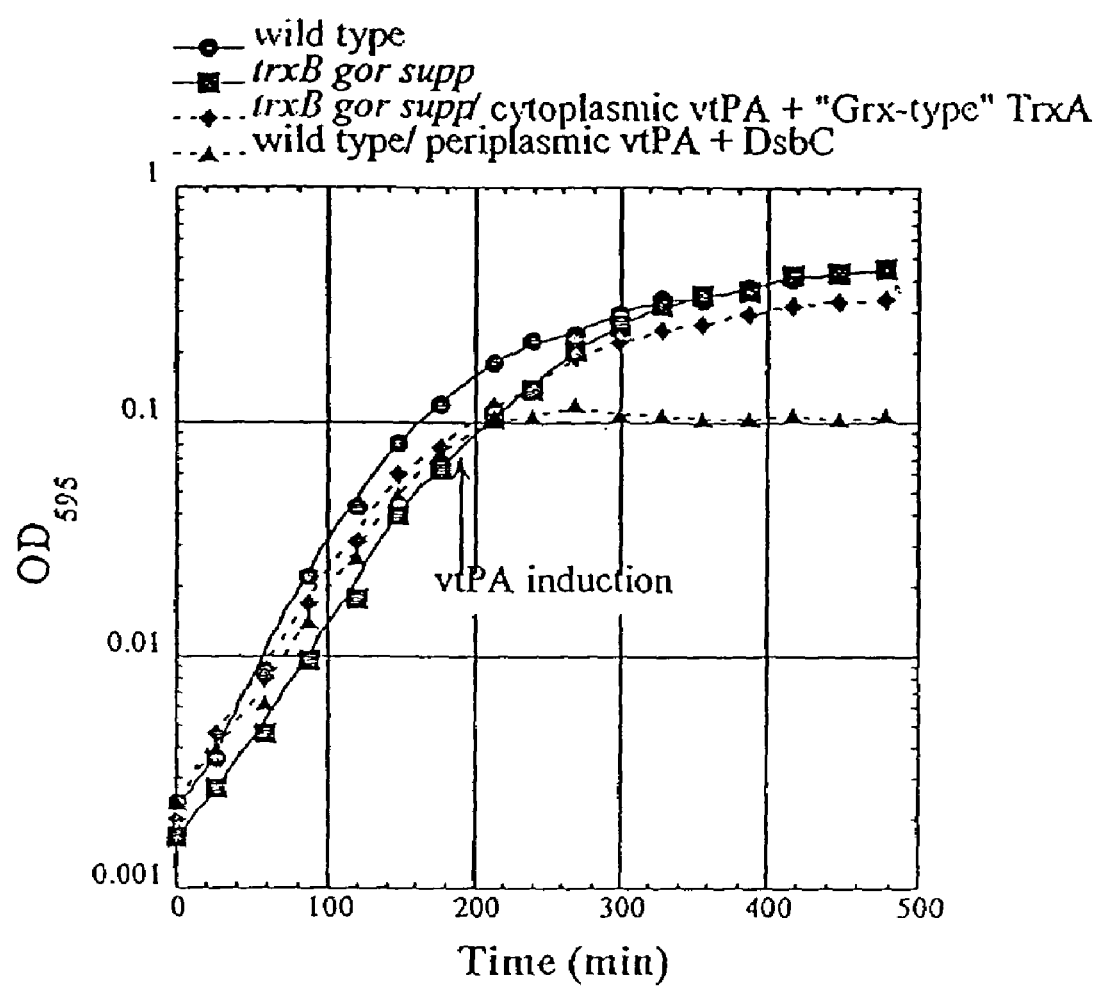
FIG. 4 is a diagram showing the growth curves of wild type E. coli (DHB4), the trxB gor supp mutant; the trxB gor supp/ cytoplasmic vtPA+"Grx-type" TrxA mutant; and the wild type/periplasmic vtPA+DsbC mutant, and the time at which production of vPA was induced.

The growth rate of FA113/pTrcvtPA/pFA5 was compared to that of wild type DHB4 and FA113. Expression of vtPA was induced at late log phase as described above, and optical density was measured in a microtiter plate reader. The results, which are shown in FIG. 4, indicate that bacterial growth of FA113 is not affected by the expression of a heterologous polypeptide.

It was of interest to compare the formation of protein disulfides in the cytosol of the strain FA113 relative to a strain with the trxB gor phenotype that had not accumulated suppressor mutations. A direct comparison of the yields of disulfide-bonded proteins in FA113 and the parental strain WP778 is not meaningful because of the dramatic difference in the growth rate of the two strains. Therefore, the strain FA222 in which the trxB gene was placed under the control of the arabinose promoter and which also contained the gor allele of FA113, was constructed as follows. Strain FA222 was derived from strain FA196, which was constructed as follows: a 1.0 kb fragment of DNA upstream of trxB was first amplified by PCR, and a 441 bp fragment was generated by digestion with NsiI. This 441 bp fragment was cloned into the NsiI site of a pBAD33 vector (Guzman, et al. (1995) *J. Bacteriol.* 177: 4121) with trxB cloned under the control of the arabinose promoter. The complete construct containing the 441 bp upstream region, the araC repressor gene and the arabinose controlled trxB allele was subcloned into the vector pK0V (obtained from G. Church, Harvard Medical School) followed by integration into the chromosome of *E. coli* DHB4 using the published procedure of Link et al. (Link, et al. (1997) *J. Bacteriol.* 179: 6228), generating FA196. P1 transduction of the gor522...mini-Tn10 allele (Prinz, et al. (1997) *J. Biol. Chem.* 272: 15661) to FA196 resulted in strain FA222.

The FA222 strain grows well in the presence of arabinose but exhibits a trxB gor phenotype when transferred to growth media lacking arabinose. Under these conditions, the accumulation of mouse urokinase in the cytosol of FA222 was comparable to that obtained in FA113. Thus, while the suppressor mutation alleviates the growth defect of trxB gor, it does not interfere with disulfide bond formation in the cytoplasm.

Example 4

Proper and Efficient Disulfide Bond Formation of OxyR in FA113

Exposure of *E. coli* to elevated concentrations of hydrogen peroxide or diamide renders the cytoplasm more oxidizing and, among other things, results in the formation of a disulfide bond in the transcription factor OxyR. The oxidized form of OxyR activates the transcription of trxC encoding thioredoxin 2 and several other genes that play a role in protecting the cell from oxidative damage (Zander, et al. (1998) *Methods Enzymol.* 290: 59) (Ritz, et al. (2000) *J. Biol. Chem.* 275: 2505). FA113 exhibited nearly full activation of OxyR as judged by the expression of TrxC and the level of oxyS RNA. Thus, proper disulfide bonds are formed in OxyR in FA113.

Example 5

Oxidized Alkaline Phosphatase Accumulates in the Cytoplasm of FA113 Cells

Pulse-chase experiments were carried out to determine the rate of protein oxidation in signal sequenceless alkaline phosphatase. *E. coli* alkaline phosphatase contains 2 disulfide bonds linking cysteines that are consecutive in the primary sequence, a property referred to as linear cysteine connectivity.

*E. coli* DHB4 expressing alkaline phosphatase devoid of signal sequence (plasmid pAID135) was constructed as follows (Derman et al. (1993) *EMBO J.* 12:879). Cells were diluted 1:100 from overnight cultures into M63 supplemented with all 18 amino acids except methionine and cysteine and grown at 37° C. When the cells reached an $OD_{600}$ of 0.2, IPTG was added to 2 mM to induce expression of alkaline phosphatase. The pulse chase was started by the addition of [$^{35}$S]methionine. After one minute, unlabeled methionine at 0.1% w/v (final concentration) was added and subsequently, samples were collected at the indicated time points (see FIG. 5) and mixed with 0.1 M iodoacetamide. The alkaline phosphatase was then immunoprecipitated and separated by native PAGE, such that the oxidized form (ox) was distinguished from the reduced form (red). OmpA was used as an internal standard.

Figure 5:
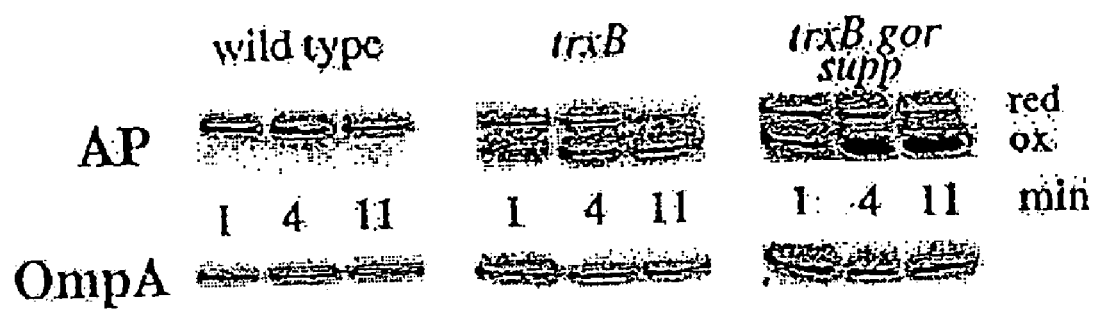
FIG. 5 shows the amount of biologically active (oxidized, as opposed to reduced) alkaline phosphatase produced in DHB4 (wild type), WP597 (trxB), and FA113 (trxB gor supp) transformed with plasmid pAID135, produced during a pulse/chase experiment at 1, 4, or 11 minutes post-chase.

The results, which are presented in FIG. 5, show that, in FA113, about 50% of the alkaline phosphatase was oxidized within one minute and was more than 95% complete after 11 minutes. The kinetics of disulfide bond formation in the trxB gor supp strain were slightly faster than in a trxB mutant. In contrast, no oxidized alkaline phosphatase accumulated in the wild type strain even after 11 minutes.

Thus, properly formed and oxidized alkaline phosphatase forms in the cytoplasm of the TrxB gor supp mutant FA113.

Example 6

Coexpression of a Variant of a Thioredoxin Variant Significantly Improves Disulfide Bond Formation Stewart et al. (Stewart, et al. (1998) *EMBO J.* 17: 5543) have shown that disruption of trxB results in an accumulation of oxidized thioredoxins which can then act as oxidases, the reverse of their normal role. Likewise, in FA113, TrxA expressed from the chromosome was present solely in the oxidized form. We examined the effect of high level expression of TrxA and TrxA mutant proteins with varying redox potentials on the folding of the more complex multi-disulfide proteins, namely vtPA and tPA. The redox potential of most cysteine oxidoreductases, including TrxA, is strongly influenced by the sequence of the dipeptide within the CXXC (SEQ ID NO: 1) active site motif (Mossner, et al. (1999) *J. Biol. Chem.* 274: 25254; Mossner, et al. (1998) *Protein Sci.* 7: 1233; Grauschopf, et al. (1995) *Cell* 83: 947). TrxA with a wild type active site (-CGPC-; SEQ ID NO: 2) and five mutants with varying redox potentials (see below) were cloned into plasmid pBAD33 (Gunzman et al. (1995) *J. Bacteriol.* 177:4121) under the control of the araBAD promoter and transformed into FA113 together with a compatible expression vector for vtPA or full length tPA synthesis.

The active site mutants of wild type TrxA that were used were as follows: -CGSC- (SEQ ID NO: 3); -CPYC- (SEQ ID NO: 4), which is the active site found in wild type Grx proteins; --CPHC- (SEQ ID NO: 5), which is the active site found in the wild type DsbA protein; -CGHC- (SEQ ID NO: 6), which is the active site found in the wild type rat protein disulfide isomerase (PDI); and -CGPA- (SEQ ID NO: 7).

Thioredoxin 1 (TrxA) and active-site mutants were amplified from the constructs of Huber et al. (1986) *J. Biol. Chem.* 261: 15006, and Mossner et al. (1999) *J. Biol. Chem.* 274: 25254 and Mossner et al. (1998) *Protein Sci.* 7:1233. Rat PDI was amplified from a construct of De Sutter et al. (1994) *Gene* 141:163.

The transformed cells were then induced with arabinose followed by addition of IPTG 30 minutes later to initiate synthesis of the tPA protein, and the yield of active tPA was analyzed three hours later by an indirect assay for plasminogen activation employing a chromogenic plasmin substrate (see Example 3). Activity has been normalized to the value obtained from vtPA expressed alone in FA113.

Western blot analysis was undertaken as a control for the amount of TrxA protein and variants expressed in each strain. Anti-TrxA antibodies were purchased from Sigma (St. Louis, Mo.). The blots indicated that TrxA and the TrxA variants accumulated to the same level at steady state.

The in vivo redox states of TrxA and the "Grx-like" TrxA variant were assayed by derivatization of free thiols by 4-acetamido-4'-maleimidyl-stilbene-2,2'-disulfonic acid (Molecular Probes, Eugene, Oreg.) and western blotting as described previously (Joly, et al. (1997) *Biochemistry* 36: 10067).

Figure 6:
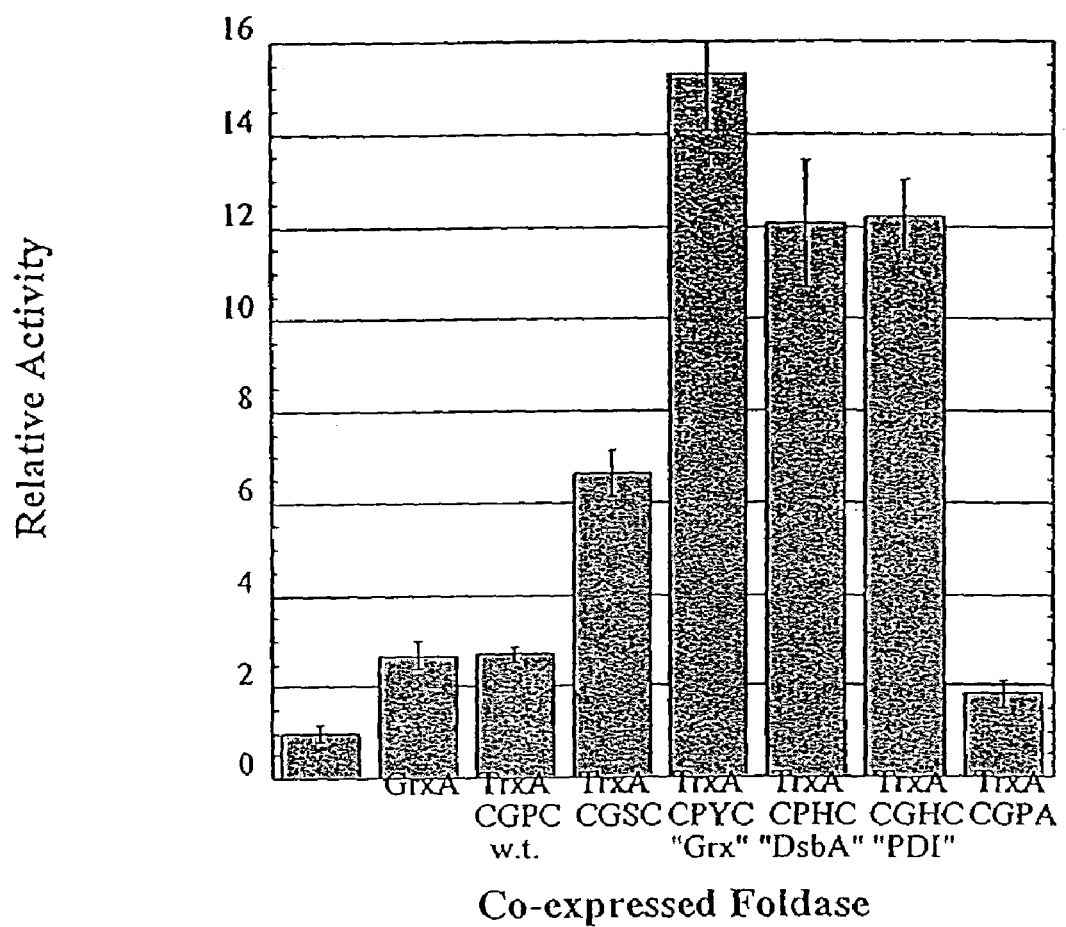
FIG. 6 is a diagram showing the activity of vtPA produced in the cytoplasm of strain FA113 (trxB gor supp) and in FA113 co-transformed with plasmids pFA2-pFA8, respectively, which encode wild type GrxA (pFA2), wildtype TrxA (pFA3), and active site mutants of TrxA (pFA4-8), relative to the activity of vtPA produced in the cytoplasm of FA113.

The results, which are shown in FIG. 6, indicate that overexpression of TrxA resulted in a modest increase in the level of active vtPA. However, co-expression of more oxidizing TrxA variants gave significantly higher accumulation of active vtPA. For example, co-expression of a more oxidizing variant with the active site of GrxA (glutaredoxin 1) resulted in active vtPA at levels 15-fold greater than the control.

Analysis of the in vivo redox state of overexpressed TrxA revealed that the wild-type enzyme is present primarily in the oxidized form, with a minor fraction in the reduced state. In contrast, the mutant with the "Grx-like" active site is mainly reduced. GrxA (glutaredoxin 1) co-expression was much less effective than the "Grx-like" TrxA, presumably a consequence of its lower redox potential and the fact that glutaredoxin is a less efficient catalyst of disulfide bond formation or reduction compared to thioredoxin (Aslund, et al. (1997) *J. Biol. Chem.* 272: 30780). Similar relative increases to those reported above were obtained with the full length tPA substrate. Interestingly, co-expression of the "Grx-like" TrxA variant significantly improved disulfide bond formation not only in FA113 but also in the trxB gshA supp strain FA112 and in the trxB mutant WP597 (DHV4 trxB::Km) as determined by fibrin clearance assays, as described in Example 3 (FIG. 3).

Thus, the results of this Example show that cotransformation of TrxB gor supp mutant with a plasmid encoding a thioredoxin variant having a higher redox potential than its wild type coutnerpart significantly increases the production of proteins containing multiple disulfide bonds in the cytoplasm of these cells.

Example 7

Coexpression of a Disulfide Bond Isomerase Greatly Increases Production of Proteins with Multiple Disulfide Bonds This Example shows that causing DsbC to be localized to the cytoplasm enhances the yield of properly assembled disulfide-containing proteins and compares the accumulation of properly formed tPA in the periplasm and cytoplasm of wild type and trxB gor supp mutants co-transformed with an additional catalyst of disulfide bond isomerization.

The folding of proteins containing multiple disulfide bonds with non-linear connectivities is greatly assisted by the addition of catalysts that enhance the rate of disulfide bond isomerization. In the *E. coli* periplasm, the formation of active urokinase and tPA is critically dependent on the DsbC disulfide isomerase activity (Qiu, et al., (1998) *Appl. Environ. Microbiol.* 64: 4891; Rietsch, et al. (1997) *J. Bacteriol.* 179: 6602). A version of DsbC without a signal sequence (amino acids 2-20) was constructed and placed behind the araBAD promoter in plasmid pBAD33 (araBAD promoter, $Cm^R$, pACYC ori; Guzman et al. (1995) *J. Bacteriol.* 177:4121) and an optimized ribosome binding site to achieve efficient translation, to yield plasmid pBADSSdsbC. A version of DsbA without a signal sequence (amino acids 2-19) was constructed and placed behind the araBAD promoter in plasmid pBAD33 and an optimized ribosome binding site, to yield plasmid pBADSSdsbA. Anti-DsbC antibodies were from John Joly (Genentech, South San Francisco, Calif.).

Figure 7:
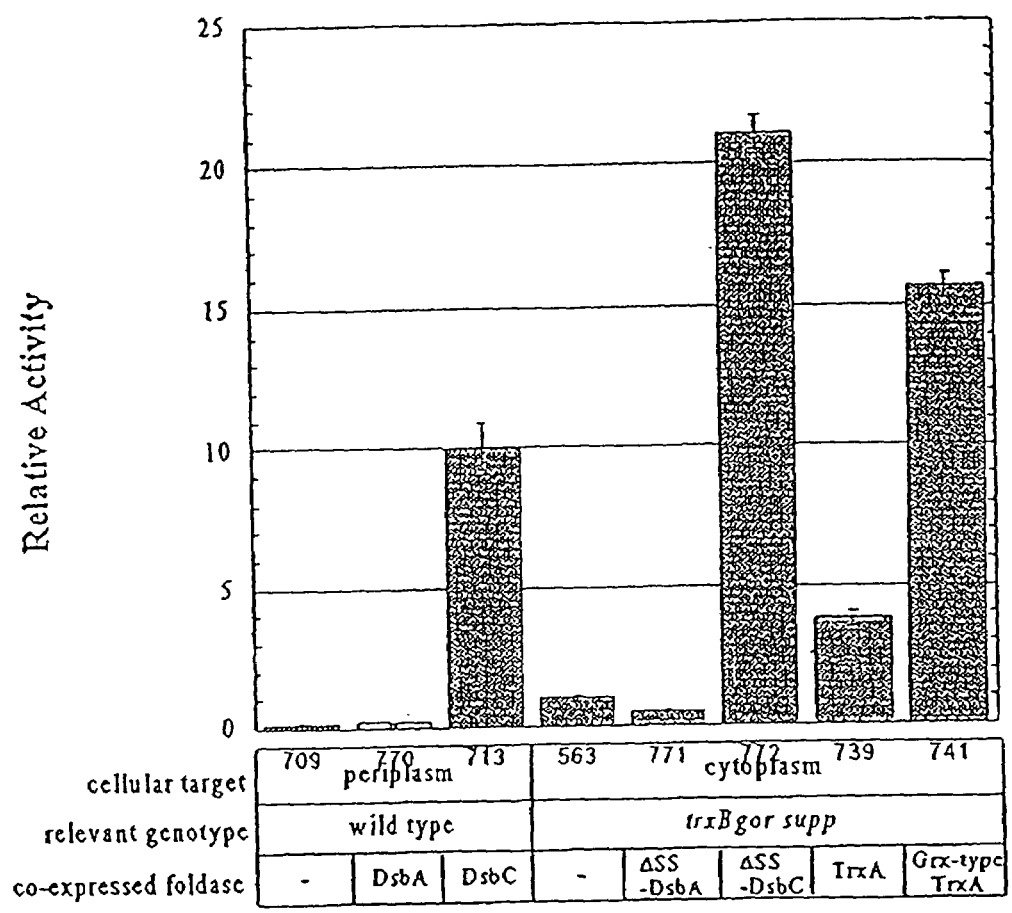
FIG. 7 is a diagram showing the activity of vtPA secreted to the periplasm of DHB4 (wild type), or in the cytoplasm of FA113 (trxB gor supp) that were cotransformed with plasmids pBADdsbA, pBADdsbC, pBADSSdsbA, pBADSSdsbC, pFA3 (TrxA), and pFA5 ("Grx-type" TrxA).

DsbC overexpressed in the cytoplasm of FA113 was found predominantly in a form where its structural disulfide had formed, but the active site was reduced. A 20-fold increase in vtPA activity was observed, corresponding to the highest accumulation of active protein in this study (FIG. 7). In contrast, co-expression of DsbA under identical conditions actually reduced the accumulation of active vtPA. The effect of the eukaryotic rat PDI (plasmid pBADrPDI consisting of mature rat PDI in pBAD33 with optimized RBS) expressed in the cytoplasm was also evaluated, but the increase in vtPA activity compared to the control cells without any foldase overexpression was marginal.

It is instructive to compare the formation of protein disulfide bonds following secretion in the periplasm of a wild type strain or in the cytoplasm of FA113. For this purpose, the vtPA gene was fused to a bacterial signal peptide from the heat stable enterotoxin II. For periplasmic expression, vtPA as well as the full length tPA were targeted for secretion by fusion to the heat-stable enterotoxin II signal sequence, referred to as "StII leader" (see, Qiu, et al. (1998) *Appl. Environ. Microbiol.* 64: 4891), to yield plasmids pTrcStI-IvtPA and pTrcStIItPA, respectively. Transformation of each of these plasmids into the bacterial strains and selection of positive clones was performed as described above.

Secretion of vtPA in the periplasm of FA113 resulted in a lower yield of active protein relative to DHB4. However, when vtPA was expressed in the cytoplasm of FA113 a higher level of active protein was obtained compared to that obtained in the periplasm of the wild type counterpart, DHB4 (FIG. 7, columns 1 and 4). Analysis by Western blotting revealed that the total level of tPA accumulation at steady state was approximately the same in the cytoplasm of FA113 and in the periplasm of DHB4. The amount of active vtPA in the periplasm of DHB4 could be increased by more than two orders of magnitude by co-expression of periplasmic DsbC. Co-expression of a signal sequenceless DsbC with vtPA in the cytoplasm of the trxB gor supp strain resulted in even higher accumulation of correctly folded protein. Under these conditions the level of active vtPA represented a 2-fold increase relative to periplasmic expression and a 200-fold increase compared to expression in the cytoplasm of DHB4. Moreover, whereas high level expression of DsbC and vtPA in the periplasm resulted in growth arrest, cytoplasmic expression did not have any appreciable effect on cell growth.

Thus, these new strains grow normally, even though the cytoplasm is highly oxidizing, and favor the formation of disulfide bonds in certain proteins with an efficiency even higher than that of the periplasm. For all the model eukaryotic proteins including the highly complex full length tPA, expression in the cytoplasm of the new strains resulted in appreciable yields of active protein exceeding that which could be obtained by periplasmic expression.

Example 8

The Suppressor Mutation in FA113 is Localized in the Alkyl Hydroperoxidase Subunit ahpC This example describes the identification of the suppressor mutation in FA113, i.e., the mutation allowing this *E. coli* strain to grow similarly to the wild type *E. coli*, by genetic mapping techniques, DNA sequencing and a series of strain constructions, essentially as described in including the technique described in Kleckner et al. (1991) *Meth. Enzym.* 204: 139. The suppressor mutation was mapped to a region near the ahpC,F gene cluster, using linkage to a transposon insertion in the chromosome. These studies show that the mutation alters the gene ahpC which encodes the peroxidase subunit of alkyl hydroperoxidase.

A transposon, called Tn10, carrying chloramphenicol resistance, was allowed to insert randomly around the bacterial chromosome of the strain FA113. This was made possible by infecting the cell with a lambda phage, λNK1324, carrying the transposon which is able to transpose from the phage genome to the bacterial genome. This procedure yielded a collection of derivatives of FA113, each of which had a transposon at a different position in the bacterial chromosome. A large collection of these derivatives was pooled, grown up and infected with the P1 phage, a phage that is able to transduce small pieces of chromosomal DNA from one strain to another.

It is expected that among the strains with transposon insertions in them, approximately 1% would have a transposon close enough to the suppressor locus that a piece of DNA could be incorporated into a P1 transducing phage carrying both a transposon and the suppressor mutation. These would be strains in which the transposon was "tightly linked" to the suppressor mutation. This P1 lysate was used to transduce a recipient *E. coli* strain that was trxB$^-$, gor$^-$ and carried a plasmid that carries a wild-type trxB gene (strain referred to as JL10), thus allowing these strains to grow in the absence of a suppressor. Since the wild-type trxB gene was under the control of the arabinose-inducible/glucose-repressible araBAD promoter, this strain expressed the wild type trxB gene when grown in the presence of arabinose, and repressed the expression of the gene in the presence of glucose.

Chloramphenicol-resistant transductants of this *E. coli* strain were obtained and screened for those that were no longer dependent on the trxB plasmid for growth. These should have the suppressor mutation in them such that the trxB, gor, supp strain can grow. The conversion to independence of this plasmid could be demonstrated by shutting off the expression of the trxB gene on the plasmid that itself was dependent on arabinose for its expression (i.e., culture in the absence of arabinose and in the presence of glucose) and subsequent loss of the plasmid resistance.

These candidates for strains in which the transposon is close to the suppressor gene were verified by making new P1 lysates on these strains and showing that these lysates could now transduce together the chloramphenicol resistance and the suppressor phenotype at high frequency. Several colonies that conferred Cm-resistance and suppressed the growth defect were obtained.

The position on the chromosome where these transposons had inserted was determined by using arbitrary polymerase chain reaction to amplify sequences that run from the transposon into the neighboring portion of the chromosome, as described in Ritz, et al. (2000) *J. Biol. Chem.* 275: 2505 and in O'Toole, G. A., Kolter, R. (1998) *Mol. Microbiol.* 28:449-461. The sequence of the chromosomal region determined in this way indicated exactly where the transposon has inserted in the chromosome since the entire sequence of the *E. coli* genome is known. This analysis indicated that all of the insertions mapped between minutes 13 and 14, i.e., a region close to the ahpC,F locus.

Sequence analysis of the entire locus, i.e., the ahpC and ahpF genes, from a wild type and 10 different suppressor strains revealed the presence of a mutation in the ahpC gene. This mutation lies in a repeat sequence of 4 TCT triplets in the gene (see FIG. 8A). The mutation amplifies this sequence with an additional repeat of the triplet, resulting in the insertion of a phenylalanine (codon 38) 9 amino acids from the active site cysteine (codon C47) of AhpC. This mutant is referred to as ahpC*.

FIG. 8B shows that the region of the protein that contains the mutation is highly conserved in homologous proteins in other microorganisms and in the corresponding human gene (TSA).

Example 9

AhpC* Restores Normal Growth to a trxB gor Double Mutant

This example demonstrates that the mutational change in AhpC was necessary and sufficient to suppress the growth defect of the double mutant JL10.

The open reading fromes coding for ahpCF were amplified from the chromosome of the wild type and the FA113 mutant by PCR and cloned into the pACYC derivative pLAC-YC. Constructs containing either the entire operon or just the ahpC-gene (wild type or mutant) were transformed into JL10 and DR456, in which in addition to the trxB and gor mutations, the ahpCF locus is also inactivated. DR456 is also referred to as "trxB gor ahpCF::Km mutant". Growth of each of these strains was determined on rich medium (NZ).

The results, which are shown in Table 2, indicate that AhpC* is required to restore normal growth in a trxB gor strain (having an inactivating mutation in trxB and gor), thus indicating that the mutation identified in Example 8 is indeed responsible for the restoration of the ability of this strain to grow similarly to a corresponding wild type strain. In addition, since the trxB gor mutants have a wild type AhpC gene, the suppressor mutation in AhpC* is dominant.

TABLE 2

Ability of strains to grow on NZ

| Relevant genotype | Gene(s) introduced | Growth on NZ |
| --- | --- | --- |
| trxB gor | | No |
| trxB gor ahpCF::Km | | No |
| trxB gor | pLAC-ahpCF | No |
| trxB gor | pLAC-ahpC | No |
| trxB gor | pLAC-ahpF | No |
| trxB gor | pLAC-ahpC*F | Yes |
| trxB gor | pLAC-ahpC* | Yes |
| trxB gor ahpCF::Km | pLAC-ahpC | No |
| trxB gor ahpCF::Km | pLAC-ahpF | No |
| trxB gor ahpCF::Km | pLAC-ahpC*F | Yes |
| trxB gor ahpCF::Km | pLAC-ahpC* | No |

The results also indicate that AhpF is required for the suppressor effect of the mutation in AhpC*, since introduction of pLAC-ahpC* alone in the strain that is deficient in AhpC and AhpF (trxB gor ahpCF:Km) does not allow growth of the strain in NZ. Thus, both AhpC* and AhpF are required to suppress DR456.

Thus, the results of this example proved that the addition of a single amino acid to AhpC abolishes the severe growth defect of strains such as FA113. In addition, the results indicated that the effect of AhpC* is dominant over the wild-type allele.

Example 10

AhPC* has Lost its Peroxidase Activity

This example demonstrates that the mutation in AhpC* eliminates essentially all of its peroxidase activity.

To determine whether AhpC* retained its original peroxidase function, e.g., its ability, together with AhpF, to confer increased resistance to alkyl peroxides in vivo, the following test was performed. Each of the operons AhpCF and AhpC*F were introduced into the high copy number plasmid pBAD18 Km under the control of the araBAD promoter and introduced into wild type E. coli. As expected, the E. coli strain containing the plasmid with the AhpCF operon exhibited increased resistance to cumene hydroperoxide (CuHP) relative to E. coli that contained a control plasmid that does not contain an AhpCF operon (see Table 3). As indicated in the table, after a 10 min exposure to 5 µM CuHP, a 10-times greater fraction of cells survived (3.2%) as compared to a vector-only control (pLAC-YC) (0.3%). The mutant AhpC* (pLAC-C*F) on the other hand did not exhibit any significant peroxidase activity as the fraction of surviving cells was the same as in the control (0.3%). Both, AhpC and AhpC* were expressed at similarly high levels, as indicated by Coomassie stained gels.

TABLE 3

Percentage of E. coli cells alive after incubation in CuHP

| Relevant genotype | plasmid introduced | CuHP survival (%) |
| --- | --- | --- |
| Wt | pLAC-YC | 0.3 |
| Wt | pLAC-ahpCF | 3.2 |
| Wt | pLAC-C*F | 0.3 |

Thus, expression of AphC* reduces essentially all of the ability of a wild type E. coli strain to survive in oxidizing condition.

The OxyR-dependent stress response in strains containing either ahpC or ahpC* was also determined. This was undertaken by introducing into various E. coli strains described above a plasmid including a trxC'-'lacZ fusion gene, in which the LacZ gene is under the control of the trxC promoter. The absence of a functional AhpCF-peroxidase system is known to increase the expression of such a construct (Ritz et al. (2000) J. Biol. Chem. 275:2505), probably because the intracellular peroxide levels are elevated in those circumstances, resulting in bindig of OxyR to the trxC promoter and activation of transcription of the lacZ gene.

TABLE 4

Expression level of beta-galactosidase in various E. coli strains

| Relevant genotype | beta-Galactosidase activity |
| --- | --- |
| Wt | 61 |
| AhpCF::Km | 393 |
| AhpCF..Tn10Cm | 79 |
| AhpC*F..Tn10Cm | 409 |

As shown in Table 4, it was found that strains expressing AhpC* (ahpC*F . . . Tn10Cm) had similar expression levels of beta-galactosidase to those obtain with a strain that does not have a functional AhpCF system (ahpCF::Km). These results further confirm that AhpC* has lost the ability to function as an alkyl hydroperoxidase in vivo.

Example 11

AhpC* Cannot Restore Normal Growth Without Glutathione or Glutaredoxin 1

This example demonstrates that restoration of wild type growth of a trxB gor mutant requires the activity of at least some reductases of the glutaredoxin system, but not of the thioredoxin system.

As described in the above Examples, disulfide bonds can efficiently be introduced into model proteins, such as urokinase and human tissue pasminogen activator, in trxB gor suppressor strains, even when these model proteins are expressed only in the cytoplasm of E. coli. Yet, the strains must retain some disulfide reducing capacities as electrons must be transferred to essential reductive enzymes such as ribonucleotide reductase or PAPS reductase (the latter only for growth on minimal media). To determine which reductases may be necessary in AhpC* containing strains, additional mutations were introduced into genes of the trxB gor AhpC* (JL19.2) strain, and tested these mutants for their ability to grow on rich medium in the presence of glucose (i.e., in conditions under which the expression of trxB is suppressed).

The results, which are presented in Table 5, indicate that both functional glutathione and glutaredoxin 1 are necessary to permit trxB gor ahpC* mutants to grow on rich medium, wherease none of the components of the thioredoxin branch (trxA and trxC) were required. These results indicate that AhpC* probably functions as a thiol reductase to replace at least partially glutathione oxido reductase in the double mutant.

TABLE 5

Ability of strains to grow on NZ

| Relevant genotype | Growth on rich medium |
| --- | --- |
| TrxB gor | No |
| TrxB gor ahpC* | Yes |
| TrxB gor ahpC* gshA | Yes |
| TrxB gor ahpC* grxA | Yes |
| TrxB gor ahpC* trxA trxC | Yes |

Example 12

Assay to Determine Whether AhpC* has Glutathione (Glutaredoxin) Activity

Figure 10:
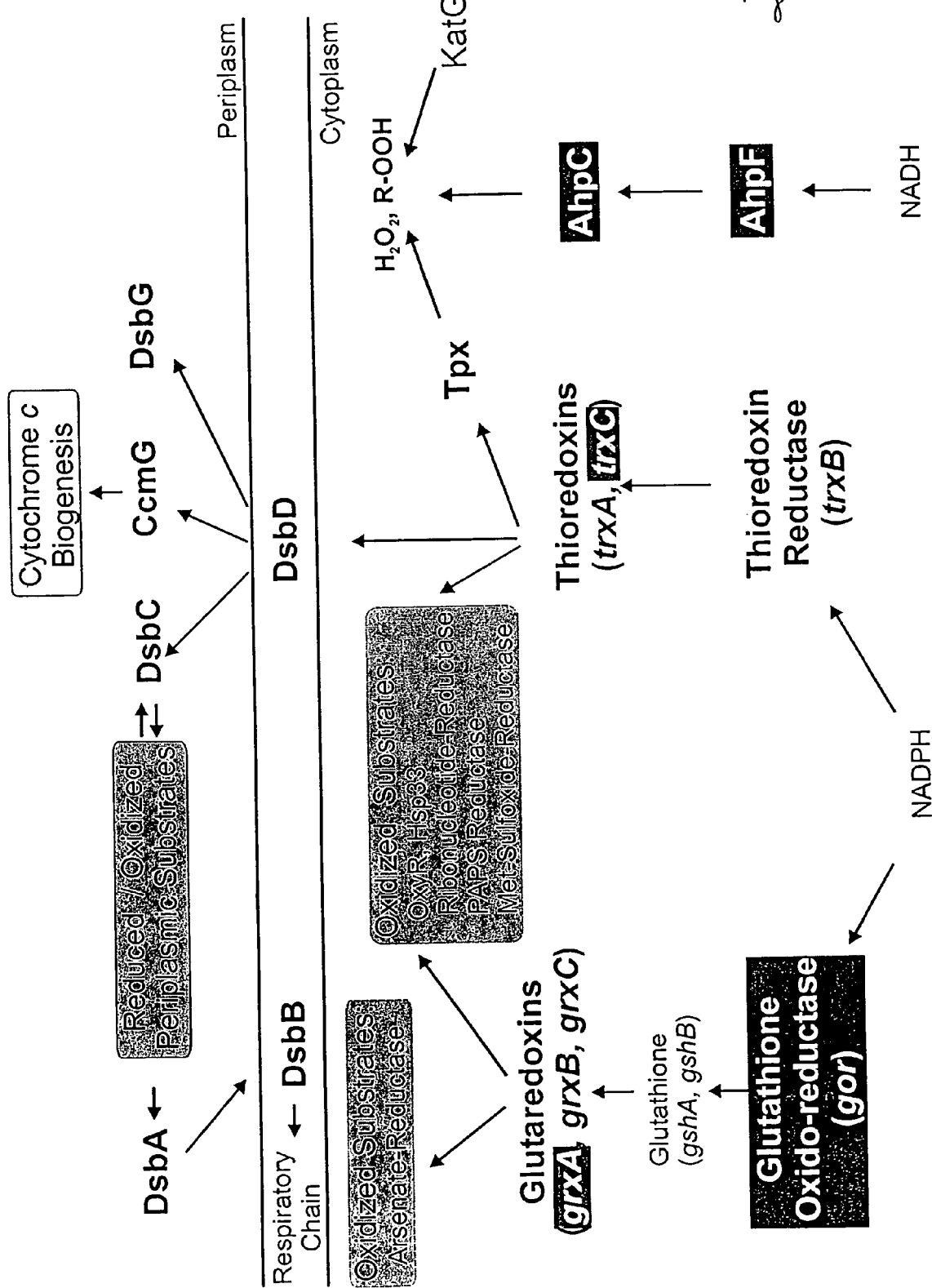
FIG. 10 is a diagram representing the reduction pathways present in a prokaryotic cell, including AhpCF.

Alkyl hydroperoxidase, product of the ahpC and ahpF genes, is a reductant that passes electrons along pairs of cysteines much as other proteins in thioredoxin and glutaredoxin pathways do (see FIGS. 9 and 10). Thus, it is not surprising that this protein might be altered to compensate for some of the defective reducing activity of the trxB,gor mutant. As described in Example 10, examination of the response of the suppressor strains to hydrogen peroxide showed that the suppressor mutation reduces the peroxidase activity of this protein. At the same time, AphC* appears to have gained a new activity, since in a strain carrying both the suppressor mutation and a wild-type copy of the ahpC, the suppressor mutation is dominant (see Examples 9 and 10). By introducing the suppressor into strains carrying an additional defect in glutaredoxin 1 expression (grxA⁻) or in glutathione biosynthesis (gshA), it was shown that the effectiveness of the suppressor is dependent on the glutathione-glutaredoxin pathway. It is thus likely the suppressor mutation restores the growth capabilities of trxB gor mutants, by altering AhpC so that it can reduce oxidized glutaredoxin 1 either directly or by reducing glutathione (see FIG. 11). Thus, the mutant enzyme restored reducing capacity to the cytoplasm sufficient to allow growth.

To determine whether AhpC* has reducing activity, in particular, that it can transfer electrons fom NADH to glutaredoxin 1 directly or via glutathione, several assays could be used. For example, one can produce and purify AhpC and AhpC* and use each of these purified proteins together with the reductase AhpF in a glutathione reductase assay. A glutathione reductase assay is well known in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A prokaryotic cell that is genetically modified to shift the redox status of the cytoplasm to a more oxidative state, which cell further expresses a heterologous polypeptide selected from the group consisting of catalysts of disulfide bond formation, disulfide bond isomerization and the combination of disulfide bond formation and disulfide bond isomerization, and which cell is further modified to increase its ability to proliferate, wherein the modification to increase its ability to proliferate is a mutation in an AhpC gene.

2. The prokaryotic cell of claim 1, wherein the expression or activity of a reductase is decreased relative to that in the corresponding wild type cell.

3. The prokaryotic cell of claim 2, wherein the reductase is selected from the group consisting of thioredoxin reductase, glutathione reductase, and glutathione.

4. The prokaryotic cell of claim 3, in which the expression or activity of a second reductase is decreased relative to that in the corresponding wild type cell.

5. The prokaryotic cell of claim 4, wherein the second reductase is selected from the group consisting of thioredoxin reductase, glutathione reductase, and glutathione.

6. The prokaryotic cell of claim 2, wherein the gene encoding the reductase is mutated.

7. The prokaryotic cell of claim 6, wherein the gene encoding the reductase contains a null mutation.

8. The prokaryotic cell of claim 5, wherein the genes encoding the first and the second reductases contain a null mutation.

9. The prokaryotic cell of claim 2, wherein the activity of the reductase is inhibited.

10. The prokaryotic cell of claim 9, wherein the activity of the reductase is inhibited by contacting the prokaryotic cell with an agent.

11. The prokaryotic cell of claim 1, wherein the modification to increase the ability of the cell to proliferate is a mutation in the endogenous ahpC gene.

12. The prokaryotic cell of claim 1, wherein the mutation is located in a region containing four triplet repeats.

13. The prokaryotic cell of claim 12, wherein the mutated ahpC protein comprises the amino acid sequence set forth in SEQ ID NO: 24.

14. The prokaryotic cell of claim 12, wherein the mutation in the ahpC gene comprises an insertion of three nucleotides in the TCT triplet repeat region
located at about codons 36-39 of an ahpC gene.

15. The prokaryotic cell of claim 14, wherein the triplet rich region of the mutated ahpC gene encodes a stretch of four phenylalanines.

16. The prokaryotic cell of claim 14, wherein the three nucleotides are TCT.

17. The prokaryotic cell of claim 15, wherein the mutated ahpC gene encodes a protein comprising SEQ ID NO: 11.

18. The prokaryotic cell of claim 17, wherein the TCT triplet rich region has the nucleotide sequence set forth in SEQ ID NO: 10.

19. The prokaryotic cell of claim 1, which is a prokaryotic cell having ATCC Designation No. PTA-938 (FA112) and further expresses a heterologous polypeptide selected from the group consisting of catalysts of disulfide bond formation, disulfide bond isomerization and the combination of disulfide bond formation and disulfide bond isomerization.

20. The prokaryotic cell of claim 1, which is a prokaryotic cell having ATCC Designation No. PTA-939 (FA113) and further expresses a heterologous polypeptide selected from the group consisting of catalysts of disulfide bond formation, disulfide bond isomerization and the combination of disulfide bond formation and disulfide bond isomerization.

21. A prokaryotic cell of claim 1, further comprising a heterologous nucleic acid encoding a protein comprising at least one cysteine that forms a disulfide bond with another cysteine.

22. The prokaryotic cell of claim 1, wherein the heterologous polypeptide is a catalyst of disulfide bond isomerization.

23. The prokaryotic cell of claim 22, wherein the reductase is selected from the group consisting of thioredoxin reductase, glutathione reductase, and glutathione.

24. The prokaryotic cell of claim 23, in which the expression or activity of a second reductase is decreased relative to that in the corresponding wild type cell.

25. The prokaryotic cell of claim 24, wherein the second reductase is selected from the group consisting of thioredoxin reductase, glutathione reductase, and glutathione.

26. The prokaryotic cell of claim 23, wherein the gene encoding the reductase is mutated.

27. The prokaryotic cell of claim 26, wherein the gene encoding the reductase contains a null mutation.

28. The prokaryotic cell of claim 24, wherein the genes encoding the first and the second reductases contain a null mutation.

29. The prokaryotic cell of claim 22, wherein the modification to increase the ability of the cell to proliferate is a mutation in the endogenous ahpC gene.

30. The prokaryotic cell of claim 29, wherein the mutation in the ahpC gene comprises an insertion of three nucleotides in the TCT triplet repeat region located at about codons 36-39 of an ahpC gene.

31. The prokaryotic cell of claim 30, wherein the three nucleotides are TCT.

32. The prokaryotic cell of claim 31, wherein the mutated ahpC protein comprises the amino acid sequence set forth in SEQ ID NO: 24.

33. A prokaryotic cell of claim 22, further comprising a heterologous nucleic acid encoding a protein comprising at least one cysteine that forms a disulfide bond with another cysteine.

34. A method for producing a protein having at least one cysteine, which forms a disulfide bond with another cysteine, comprising isolating the protein from a cell of claim 22 in which has been introduced a nucleic acid encoding the protein, which protein has at least one cysteine that forms a disulfide bond with another cysteine, and which cell has been grown under conditions in which the protein is produced.

35. The prokaryotic cell of claim 1, wherein the catalyst is a DsbC protein without a signal sequence or a variant thereof that is encoded by a nucleic acid that hybridizes to a nucleic acid encoding a DsbC protein under conditions including a wash in 0.2×SSC at 50° C., wherein the variant acts as a catalyst selected from the group consisting of catalysts of disulfide bond formation, disulfide bond isomerization and the combination of disulfide bond formation and disulfide bond isomerization.

36. The prokaryotic cell of claim 1, wherein the catalyst is a variant of a protein of the thioredoxin superfamily having a redox potential that is higher than that of its wild type counterpart.

37. The prokaryotic cell of claim 36, wherein the variant is a "Grx" variant of thioredoxin A.

38. The prokaryotic cell of claim 35, wherein the catalyst is a DsbC protein without a signal sequence.

39. A method for producing a protein having at least one cysteine, which forms a disulfide bond with another cysteine, comprising isolating the protein from a cell of claim 1 in which has been introduced a nucleic acid encoding the protein, which protein has at least one cysteine that forms a disulfide bond with another cysteine, and which cell has been grown under conditions in which the protein is produced.

* * * * *

SEQUENCE LISTING

```
<160> NUMBER OF SEQ ID NOS: 24

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:
      Illustrative motif
<220> FEATURE:
<221> NAME/KEY: MOD_RES
<222> LOCATION: (2)..(3)
<223> OTHER INFORMATION: Any amino acid

<400> SEQUENCE: 1

Cys Xaa Xaa Cys
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      variant motif
```

```
<400> SEQUENCE: 2

Cys Gly Pro Cys
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      variant motif

<400> SEQUENCE: 3

Cys Gly Ser Cys
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      variant motif

<400> SEQUENCE: 4

Cys Pro Tyr Cys
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      variant motif

<400> SEQUENCE: 5

Cys Pro His Cys
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      variant motif

<400> SEQUENCE: 6

Cys Gly His Cys
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      variant motif

<400> SEQUENCE: 7

Cys Gly Pro Ala
  1

<210> SEQ ID NO 8
<211> LENGTH: 48
<212> TYPE: DNA
```

<213> ORGANISM: Escherichia coli
<220> FEATURE:
<221> NAME/KEY: CDS
<222> LOCATION: (1)..(48)

<400> SEQUENCE: 8

```
tgg agc gtc ttc ttc ttc tac ccg gct gac ttt act ttc gta tgc ccg    48
Trp Ser Val Phe Phe Phe Tyr Pro Ala Asp Phe Thr Phe Val Cys Pro
 1               5                  10                  15
```

<210> SEQ ID NO 9
<211> LENGTH: 16
<212> TYPE: PRT
<213> ORGANISM: Escherichia coli

<400> SEQUENCE: 9

```
Trp Ser Val Phe Phe Phe Tyr Pro Ala Asp Phe Thr Phe Val Cys Pro
 1               5                  10                  15
```

<210> SEQ ID NO 10
<211> LENGTH: 51
<212> TYPE: DNA
<213> ORGANISM: Escherichia coli
<220> FEATURE:
<221> NAME/KEY: CDS
<222> LOCATION: (1)..(51)

<400> SEQUENCE: 10

```
tgg agc gtc ttc ttc ttc tac ccg gct gac ttt act ttc gta tgc        48
Trp Ser Val Phe Phe Phe Tyr Pro Ala Asp Phe Thr Phe Val Cys
 1               5                  10                  15 ccg                                                                51
Pro
```

<210> SEQ ID NO 11
<211> LENGTH: 17
<212> TYPE: PRT
<213> ORGANISM: Escherichia coli

<400> SEQUENCE: 11

```
Trp Ser Val Phe Phe Phe Tyr Pro Ala Asp Phe Thr Phe Val Cys
 1               5                  10                  15

Pro
```

<210> SEQ ID NO 12
<211> LENGTH: 32
<212> TYPE: PRT
<213> ORGANISM: Escherichia coli

<400> SEQUENCE: 12

```
Arg Trp Ser Val Phe Phe Phe Tyr Pro Ala Asp Phe Thr Phe Val Cys
 1               5                  10                  15

Pro Thr Glu Leu Gly Asp Val Ala Asp His Tyr Glu Glu Leu Gln Lys
             20                  25                  30
```

<210> SEQ ID NO 13
<211> LENGTH: 32
<212> TYPE: PRT
<213> ORGANISM: Salmonella typhi

<400> SEQUENCE: 13

```
Arg Trp Ser Val Phe Phe Phe Tyr Pro Ala Asp Phe Thr Phe Val Cys
 1               5                  10                  15

Pro Thr Glu Leu Gly Asp Val Ala Asp His Tyr Glu Glu Leu Gln Lys
```

<210> SEQ ID NO 14
<211> LENGTH: 32
<212> TYPE: PRT
<213> ORGANISM: Pseudomonas putida

<400> SEQUENCE: 14

Lys Trp Ser Val Val Phe Phe Tyr Pro Ala Asp Phe Thr Phe Val Cys
 1               5                  10                  15

Pro Thr Glu Leu Gly Asp Leu Ala Asp Asn Tyr Ala Glu Phe Gln Lys
            20                  25                  30

<210> SEQ ID NO 15
<211> LENGTH: 32
<212> TYPE: PRT
<213> ORGANISM: Staphylococcus mutans

<400> SEQUENCE: 15

Lys Trp Ala Val Phe Cys Phe Tyr Pro Ala Asp Phe Ser Phe Val Cys
 1               5                  10                  15

Pro Thr Glu Leu Gly Asp Leu Gln Glu Gln Tyr Ala Thr Leu Gln Ser
            20                  25                  30

<210> SEQ ID NO 16
<211> LENGTH: 32
<212> TYPE: PRT
<213> ORGANISM: Bacillus subtilis

<400> SEQUENCE: 16

Gln Trp Ser Val Phe Cys Phe Tyr Pro Ala Asp Phe Ser Phe Val Cys
 1               5                  10                  15

Pro Thr Glu Leu Glu Asp Leu Gln Glu Gln Tyr Ala Ala Leu Lys Glu
            20                  25                  30

<210> SEQ ID NO 17
<211> LENGTH: 32
<212> TYPE: PRT
<213> ORGANISM: Staphylococcus aureus

<400> SEQUENCE: 17

Ser Trp Ser Val Val Cys Phe Tyr Pro Ala Asp Phe Ser Phe Val Cys
 1               5                  10                  15

Pro Thr Glu Leu Glu Asp Leu Gln Asn Gln Tyr Glu Glu Leu Gln Lys
            20                  25                  30

<210> SEQ ID NO 18
<211> LENGTH: 32
<212> TYPE: PRT
<213> ORGANISM: Treponema pallidum

<400> SEQUENCE: 18

Ser Trp Ala Val Phe Met Phe Tyr Pro Ala Asp Phe Thr Phe Val Cys
 1               5                  10                  15

Pro Thr Glu Leu Ala Asp Leu Ala Arg Val Tyr Pro Ser Phe Val Glu
            20                  25                  30

<210> SEQ ID NO 19
<211> LENGTH: 32
<212> TYPE: PRT
<213> ORGANISM: Aquifex aeolicus

<400> SEQUENCE: 19

```
Lys Trp Val Ile Leu Phe Phe Tyr Pro Ala Asp Tyr Thr Phe Val Cys
 1               5                  10                  15

Pro Thr Glu Leu Ala Asp Leu Ala Glu Lys Tyr Asp Glu Leu Lys Glu
             20                  25                  30

<210> SEQ ID NO 20
<211> LENGTH: 32
<212> TYPE: PRT
<213> ORGANISM: Homo sapiens

<400> SEQUENCE: 20

Lys Tyr Val Val Leu Phe Phe Tyr Pro Leu Asp Phe Thr Phe Val Cys
 1               5                  10                  15

Pro Thr Glu Ile Ile Ala Phe Thr Thr Val Lys Arg Thr Ser Ala Lys
             20                  25                  30

<210> SEQ ID NO 21
<211> LENGTH: 1483
<212> TYPE: DNA
<213> ORGANISM: Escherichia coli
<220> FEATURE:
<221> NAME/KEY: CDS
<222> LOCATION: (195)..(758)

<400> SEQUENCE: 21
aagggtagtt cagattacac ggtcacctgg aaaggggggcc attttacttt ttatgcgctg      60
gcggtgcaaa gttcacaaag ttgtcttacg aaggttgtaa ggtaaaactt atcgatttga     120
taatggaaac gcattaccgg aatcggcaaa aattggttac cttacatctc atcgaaaaca     180
cggaggaagt atag atg tcc ttg att aac acc aaa att aaa cct ttt aaa       230
              Met Ser Leu Ile Asn Thr Lys Ile Lys Pro Phe Lys
                   1               5                  10 aac cag gca ttc aaa aac ggc gaa ttc atc gaa atc acc gaa aaa gat       278
Asn Gln Ala Phe Lys Asn Gly Glu Phe Ile Glu Ile Thr Glu Lys Asp
             15                  20                  25 acc gaa ggc cgc tgg agc gtc ttc ttc tac ccg gct gac ttt act           326
Thr Glu Gly Arg Trp Ser Val Phe Phe Phe Tyr Pro Ala Asp Phe Thr
         30                  35                  40 ttc gta tgc ccg acc gaa ctg ggt gac gtt gct gac cac tac gaa gaa       374
Phe Val Cys Pro Thr Glu Leu Gly Asp Val Ala Asp His Tyr Glu Glu
 45                  50                  55                  60 ctg cag aaa ctg ggc gta gac gta tac gca gta tct acc gat act cac       422
Leu Gln Lys Leu Gly Val Asp Val Tyr Ala Val Ser Thr Asp Thr His
                 65                  70                  75 ttc acc cac aaa gca tgg cac agc agc tct gaa acc atc gct aaa atc       470
Phe Thr His Lys Ala Trp His Ser Ser Ser Glu Thr Ile Ala Lys Ile
             80                  85                  90 aaa tat gcg atg atc ggc gac ccg act ggc gcc ctg acc cgt aac ttc       518
Lys Tyr Ala Met Ile Gly Asp Pro Thr Gly Ala Leu Thr Arg Asn Phe
         95                 100                 105 gac aac atg cgt gaa gat gaa ggt ctg gct gac cgt gcg acc ttc gtt       566
Asp Asn Met Arg Glu Asp Glu Gly Leu Ala Asp Arg Ala Thr Phe Val
    110                 115                 120 gtt gac ccg cag ggt atc atc cag gca atc gaa gtt acc gct gaa ggc       614
Val Asp Pro Gln Gly Ile Ile Gln Ala Ile Glu Val Thr Ala Glu Gly
125                 130                 135                 140 att ggc cgt gac gcg tct gac ctg ctg cgt aaa atc aaa gca gca cag       662
Ile Gly Arg Asp Ala Ser Asp Leu Leu Arg Lys Ile Lys Ala Ala Gln
                145                 150                 155 tac gta gct tct cac cca ggt gaa gtt tgc ccg gct aaa tgg aaa gaa       710
```

```
                      Tyr Val Ala Ser His Pro Gly Glu Val Cys Pro Ala Lys Trp Lys Glu
                                      160                 165                 170
ggt gaa gca act ctg gct ccg tct ctg gac ctg gtt ggt aaa atc taa           758
Gly Glu Ala Thr Leu Ala Pro Ser Leu Asp Leu Val Gly Lys Ile
            175                 180                 185 atttccttag tctttcacgc atagcggcgt tgcgtcgccc gctcacccgg tcacttactt         818
gtgtaagctc ccggggattc acagctagcg ccttgctctg acgcgaaata cttcggaaat         878
tcacctaatt cttcgggtgc tgcggcgcat tttcttcccc gcaccatgat gcaagctgca         938
tccaggtagc cgcagaggcc gcttgcatga tgatgtttaa gagcccagga gataaacatg         998
ctcgacacaa atatgaaaac tcaactcaag gcttaccttg agaaattgac caagcctgtt        1058
gagttaattg ccacgctgga tgacagcgct aaatcggcag aaatcaagga actgttggct        1118
gaaatcgcag aactgtcaga caaagtcacc tttaagaag ataacagctt gccggtgcgt         1178
aagccgtctt tcctgatcac caacccaggt tccaaccagg ggccacgttt tgcaggctct        1238
ccgctgggcc acgagttcac ctcgctggta ctggcgttgc tgtggaccgg tggtcatccg        1298
tcgaaagaag cgcagtctct gctggagcag attcgccata ttgacggtga ttttgaattc        1358
gaaacctatt actcgctctc ttgccacaac tgcccggacg tggtgcaggc gctgaacctg        1418
atgagcgtac tgaacccgcg catcaagcac actgcaattg acggcggcac cttccagaac        1478
gaaat                                                                    1483

<210> SEQ ID NO 22
<211> LENGTH: 187
<212> TYPE: PRT
<213> ORGANISM: Escherichia coli

<400> SEQUENCE: 22

Met Ser Leu Ile Asn Thr Lys Ile Lys Pro Phe Lys Asn Gln Ala Phe
  1               5                  10                  15

Lys Asn Gly Glu Phe Ile Glu Ile Thr Glu Lys Asp Thr Glu Gly Arg
             20                  25                  30

Trp Ser Val Phe Phe Phe Tyr Pro Ala Asp Phe Thr Phe Val Cys Pro
         35                  40                  45

Thr Glu Leu Gly Asp Val Ala Asp His Tyr Glu Glu Leu Gln Lys Leu
     50                  55                  60

Gly Val Asp Val Tyr Ala Val Ser Thr Asp Thr His Phe Thr His Lys
 65                  70                  75                  80

Ala Trp His Ser Ser Ser Glu Thr Ile Ala Lys Ile Lys Tyr Ala Met
                 85                  90                  95

Ile Gly Asp Pro Thr Gly Ala Leu Thr Arg Asn Phe Asp Asn Met Arg
            100                 105                 110

Glu Asp Glu Gly Leu Ala Asp Arg Ala Thr Phe Val Val Asp Pro Gln
        115                 120                 125

Gly Ile Ile Gln Ala Ile Glu Val Thr Ala Glu Gly Ile Gly Arg Asp
    130                 135                 140

Ala Ser Asp Leu Leu Arg Lys Ile Lys Ala Ala Gln Tyr Val Ala Ser
145                 150                 155                 160

His Pro Gly Glu Val Cys Pro Ala Lys Trp Lys Glu Gly Glu Ala Thr
                165                 170                 175

Leu Ala Pro Ser Leu Asp Leu Val Gly Lys Ile
            180                 185

<210> SEQ ID NO 23
```

<211> LENGTH: 1486
<212> TYPE: DNA
<213> ORGANISM: Escherichia coli
<220> FEATURE:
<221> NAME/KEY: CDS
<222> LOCATION: (195)..(761)

<400> SEQUENCE: 23

| | | |
|---|---|---:|
| aagggtagtt cagattacac ggtcacctgg aaaggggcc attttacttt ttatgcgctg | | 60 |
| gcggtgcaaa gttcacaaag ttgtcttacg aaggttgtaa ggtaaaactt atcgatttga | | 120 |
| taatggaaac gcattaccgg aatcggcaaa aattggttac cttacatctc atcgaaaaca | | 180 |
| cggaggaagt atag atg tcc ttg att aac acc aaa att aaa cct ttt aaa | | 230 |
|  Met Ser Leu Ile Asn Thr Lys Ile Lys Pro Phe Lys | | |
|  1               5                  10 | | |
| aac cag gca ttc aaa aac ggc gaa ttc atc gaa atc acc gaa aaa gat | | 278 |
| Asn Gln Ala Phe Lys Asn Gly Glu Phe Ile Glu Ile Thr Glu Lys Asp | | |
|      15                  20                  25 | | |
| acc gaa ggc cgc tgg agc gtc ttc ttc ttc tac ccg gct gac ttt | | 326 |
| Thr Glu Gly Arg Trp Ser Val Phe Phe Phe Phe Tyr Pro Ala Asp Phe | | |
|  30                  35                  40 | | |
| act ttc gta tgc ccg acc gaa ctg ggt gac gtt gct gac cac tac gaa | | 374 |
| Thr Phe Val Cys Pro Thr Glu Leu Gly Asp Val Ala Asp His Tyr Glu | | |
|  45                  50                  55                  60 | | |
| gaa ctg cag aaa ctg ggc gta gac gta tac gca gta tct acc gat act | | 422 |
| Glu Leu Gln Lys Leu Gly Val Asp Val Tyr Ala Val Ser Thr Asp Thr | | |
|              65                  70                  75 | | |
| cac ttc acc cac aaa gca tgg cac agc agc tct gaa acc atc gct aaa | | 470 |
| His Phe Thr His Lys Ala Trp His Ser Ser Ser Glu Thr Ile Ala Lys | | |
|          80                  85                  90 | | |
| atc aaa tat gcg atg atc ggc gac ccg act ggc gcc ctg acc cgt aac | | 518 |
| Ile Lys Tyr Ala Met Ile Gly Asp Pro Thr Gly Ala Leu Thr Arg Asn | | |
|      95                 100                 105 | | |
| ttc gac aac atg cgt gaa gat gaa ggt ctg gct gac cgt gcg acc ttc | | 566 |
| Phe Asp Asn Met Arg Glu Asp Glu Gly Leu Ala Asp Arg Ala Thr Phe | | |
|  110                 115                 120 | | |
| gtt gtt gac ccg cag ggt atc atc cag gca atc gaa gtt acc gct gaa | | 614 |
| Val Val Asp Pro Gln Gly Ile Ile Gln Ala Ile Glu Val Thr Ala Glu | | |
| 125                 130                 135                 140 | | |
| ggc att ggc cgt gac gcg tct gac ctg ctg cgt aaa atc aaa gca gca | | 662 |
| Gly Ile Gly Arg Asp Ala Ser Asp Leu Leu Arg Lys Ile Lys Ala Ala | | |
|                 145                 150                 155 | | |
| cag tac gta gct tct cac cca ggt gaa gtt tgc ccg gct aaa tgg aaa | | 710 |
| Gln Tyr Val Ala Ser His Pro Gly Glu Val Cys Pro Ala Lys Trp Lys | | |
|              160                 165                 170 | | |
| gaa ggt gaa gca act ctg gct ccg tct ctg gac ctg gtt ggt aaa atc | | 758 |
| Glu Gly Glu Ala Thr Leu Ala Pro Ser Leu Asp Leu Val Gly Lys Ile | | |
|          175                 180                 185 | | |
| taa atttcctag tctttcacgc atagcggcgt tgcgtcgccc gctcacccgg | | 811 |
| tcacttactt gtgtaagctc ccggggattc acagctagcg ccttgctctg acgcgaaata | | 871 |
| cttcggaaat tcacctaatt cttcgggtgc tgcggcgcat tttcttcccc gcaccatgat | | 931 |
| gcaagctgca tccaggtagc cgcagaggcc gcttgcatga tgatgtttaa gagcccagga | | 991 |
| gataaacatg ctcgacacaa atatgaaaac tcaactcaag gcttaccttg agaaattgac | | 1051 |
| caagcctgtt gagttaattg ccacgctgga tgacagcgct aaatcggcag aaatcaagga | | 1111 |
| actgttggct gaaatcgcag aactgtcaga caaagtcacc tttaaagaag ataacagctt | | 1171 |
| gccggtgcgt aagccgtctt tcctgatcac caacccaggt tccaaccagg ggccacgttt | | 1231 |

-continued

```
tgcaggctct ccgctgggcc acgagttcac ctcgctggta ctggcgttgc tgtggaccgg    1291
tggtcatccg tcgaaagaag cgcagtctct gctggagcag attcgccata ttgacggtga    1351
ttttgaattc gaaacctatt actcgctctc ttgccacaac tgcccggacg tggtgcaggc    1411
gctgaacctg atgagcgtac tgaacccgcg catcaagcac actgcaattg acggcggcac    1471
cttccagaac gaaat                                                     1486
```

<210> SEQ ID NO 24
<211> LENGTH: 188
<212> TYPE: PRT
<213> ORGANISM: Escherichia coli

<400> SEQUENCE: 24

```
Met Ser Leu Ile Asn Thr Lys Ile Lys Pro Phe Lys Asn Gln Ala Phe
  1               5                  10                  15

Lys Asn Gly Glu Phe Ile Glu Ile Thr Glu Lys Asp Thr Glu Gly Arg
                 20                  25                  30

Trp Ser Val Phe Phe Phe Tyr Pro Ala Asp Phe Thr Phe Val Cys
             35                  40                  45

Pro Thr Glu Leu Gly Asp Val Ala Asp His Tyr Glu Glu Leu Gln Lys
         50                  55                  60

Leu Gly Val Asp Val Tyr Ala Val Ser Thr Asp Thr His Phe Thr His
 65                  70                  75                  80

Lys Ala Trp His Ser Ser Glu Thr Ile Ala Lys Ile Lys Tyr Ala
                 85                  90                  95

Met Ile Gly Asp Pro Thr Gly Ala Leu Thr Arg Asn Phe Asp Asn Met
                100                 105                 110

Arg Glu Asp Glu Gly Leu Ala Asp Arg Ala Thr Phe Val Val Asp Pro
            115                 120                 125

Gln Gly Ile Ile Gln Ala Ile Glu Val Thr Ala Glu Gly Ile Gly Arg
        130                 135                 140

Asp Ala Ser Asp Leu Leu Arg Lys Ile Lys Ala Ala Gln Tyr Val Ala
145                 150                 155                 160

Ser His Pro Gly Glu Val Cys Pro Ala Lys Trp Lys Glu Gly Glu Ala
                165                 170                 175

Thr Leu Ala Pro Ser Leu Asp Leu Val Gly Lys Ile
                180                 185
```